United States Patent
Kato et al.

(10) Patent No.: US 10,743,834 B2
(45) Date of Patent: Aug. 18, 2020

(54) X-RAY IMAGE DIAGNOSTIC APPARATUS AND METHOD

(71) Applicant: Toshiba Medical Systems Corporation, Otawara-shi (JP)

(72) Inventors: Tooru Kato, Nasushiobara (JP); Hiroaki Nakai, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 221 days.

(21) Appl. No.: 15/723,824

(22) Filed: Oct. 3, 2017

(65) Prior Publication Data

US 2018/0098746 A1 Apr. 12, 2018

(30) Foreign Application Priority Data

Oct. 6, 2016 (JP) .................................. 2016-198354

(51) Int. Cl.
| | | |
|---|---|---|
| *A61B 6/00* | (2006.01) | |
| *G21K 1/10* | (2006.01) | |
| *A61B 6/03* | (2006.01) | |

(52) U.S. Cl.
CPC .............. *A61B 6/585* (2013.01); *A61B 6/032* (2013.01); *A61B 6/405* (2013.01); *A61B 6/4035* (2013.01);
(Continued)

(58) Field of Classification Search
CPC ....... A61B 6/585; A61B 6/032; A61B 6/4035; A61B 6/405; A61B 6/4233; A61B 6/4241;
(Continued)

(56) References Cited

U.S. PATENT DOCUMENTS

| | | | |
|---|---|---|---|
| 9,351,701 B2 | 5/2016 | Yamakawa et al. | |
| 2012/0087463 A1* | 4/2012 | Greenberg | ................ G01T 1/29 378/5 |

(Continued)

FOREIGN PATENT DOCUMENTS

| | | |
|---|---|---|
| JP | 2011-85479 | 4/2011 |
| JP | 2015-134106 | 7/2015 |

(Continued)

OTHER PUBLICATIONS

Hideki Kato et al., "Energy-Absorption Response of Cadmium Zinc Telluride (CdZnTe) Semiconductor Detectors to X-ray Photon Beams", T.IEE Japan, vol. 120-C, No. 12, 2000, pp. 7 (with English Abstract).

(Continued)

*Primary Examiner* — Taeho Jo
(74) *Attorney, Agent, or Firm* — Oblon, McClelland, Maier & Neustadt, L.L.P.

(57) ABSTRACT

An X-ray image diagnostic apparatus according to an embodiment includes a photon counting X-ray detector, calibration circuitry, and image generating circuitry. The photon counting X-ray detector includes a plurality of detection elements each of which is configured to detect X-rays and output a detection signal. The calibration circuitry calibrates a detection signal of each of the detection elements using a correction value calculated from a plurality of signals output from the detection elements and corresponding to a plurality of X-ray application conditions relating to continuous X-rays. The image generating circuitry generates an image using the calibrated detection signals of the detection elements.

23 Claims, 18 Drawing Sheets

(52) U.S. Cl.
CPC .......... *A61B 6/4233* (2013.01); *A61B 6/4241* (2013.01); *A61B 6/482* (2013.01); *A61B 6/5205* (2013.01); *A61B 6/54* (2013.01); *A61B 6/542* (2013.01); *G21K 1/10* (2013.01)

(58) Field of Classification Search
CPC ......... A61B 6/482; A61B 6/5205; A61B 6/54; A61B 6/542; G21K 1/10
USPC .......................................................... 378/91
See application file for complete search history.

(56) References Cited

U.S. PATENT DOCUMENTS

| | | | |
|---|---|---|---|
| 2014/0105370 A1* | 4/2014 | Yamakawa | A61B 6/025 378/207 |
| 2014/0140469 A1* | 5/2014 | Carmi | G01N 23/046 378/9 |
| 2014/0254747 A1* | 9/2014 | Saito | A61B 6/032 378/5 |
| 2014/0326894 A1* | 11/2014 | Abraham | H04N 5/32 250/394 |
| 2015/0250444 A1 | 9/2015 | Tamura | |
| 2015/0287221 A1* | 10/2015 | Takayama | G01N 23/046 382/131 |
| 2015/0346354 A1* | 12/2015 | Arakita | G01T 1/1606 378/19 |
| 2016/0073988 A1* | 3/2016 | Nagai | A61B 6/42 378/62 |
| 2016/0095564 A1* | 4/2016 | Kato | A61B 6/52 378/19 |
| 2016/0113603 A1* | 4/2016 | Schirra | A61B 6/032 250/252.1 |
| 2016/0174922 A1* | 6/2016 | Kodera | A61B 6/4035 378/37 |
| 2016/0203620 A1* | 7/2016 | Zou | A61B 6/032 378/19 |
| 2016/0282487 A1* | 9/2016 | Kawata | G01T 7/005 |
| 2016/0374629 A1* | 12/2016 | Kawata | A61B 6/032 378/19 |
| 2017/0095222 A1* | 4/2017 | Hashimoto | A61B 6/4488 |
| 2017/0285186 A1* | 10/2017 | Roessl | G01T 1/24 |
| 2018/0078233 A1* | 3/2018 | Jin | G06T 11/003 |

FOREIGN PATENT DOCUMENTS

| | | |
|---|---|---|
| JP | 2015-180859 | 10/2015 |
| JP | 2015-184116 A | 10/2015 |
| JP | 2016-19633 | 2/2016 |
| JP | 2016-067947 A | 5/2016 |

OTHER PUBLICATIONS

Japanese Office Action dated Jul. 7, 2020, issued in corresponding Japanese Patent Application No. 2016-198354.

* cited by examiner

- REFERENCE DETECTION ELEMENT (HIGH ENERGY RESOLUTION)
- STANDARD X-RAY DETECTION ELEMENT
- STANDARD X-RAY DETECTION ELEMENT (DURING APPLICATION OF X-RAYS)

- REFERENCE DETECTION ELEMENT (HIGH ENERGY RESOLUTION)
- STANDARD X-RAY DETECTION ELEMENT
- STANDARD X-RAY DETECTION ELEMENT (DURING APPLICATION OF X-RAYS)

X-RAY IMAGE DIAGNOSTIC APPARATUS AND METHOD

CROSS-REFERENCE TO RELATED APPLICATIONS

This application is based upon and claims the benefit of priority from Japanese Patent Application No. 2016-198354, filed on Oct. 6, 2016; the entire contents of which are incorporated herein by reference.

FIELD

Embodiments described herein relate generally to an X-ray image diagnostic apparatus and method.

BACKGROUND

Photon counting X-ray detectors are known X-ray detectors used in X-ray CT apparatuses. Each of X-ray detecting elements included in a photon counting X-ray detector is capable of counting incident X-ray photons, and outputting a detection signal capable of measuring an energy value (key) of each of the X-ray photons. In the case of using a photon counting X-ray detector, calibration is indispensable to calibrate variations of X-ray energy sensitivity between X-ray detecting elements.

DETAILED DESCRIPTION

The following is an explanation of an X-ray image diagnostic apparatus and method according to embodiments, with reference to drawings.

Each of the following embodiments illustrates an X-ray CT apparatus serving as an example of the X-ray image diagnostic apparatus. The X-ray CT apparatus illustrated in each of the embodiments is an apparatus capable of performing photon counting CT. Specifically, the X-ray CT apparatus illustrated in each of the following embodiments is an apparatus capable of counting X-rays transmitted through a subject using a photon counting detector, not a conventional integral-type (current mode measurement method) detector, to reconstruct X-ray CT image data with high SN ratio. The details described in one embodiment is also applied to the other embodiments in the same manner, in principle.

An X-ray image diagnostic apparatus according to an embodiment includes a photon counting X-ray detector, calibration circuitry, and image generating circuitry. The photon counting X-ray detector includes a plurality of detection elements each of which is configured to detect X-rays and output a detection signal. The calibration circuitry calibrates a detection signal of each of the detection elements using a correction value calculated from a plurality of signals output from the detection elements and corresponding to a plurality of X-ray application conditions relating to continuous X-rays. The image generating circuitry generates an image using the calibrated detection signals of the detection elements.

First Embodiment

Figure 1:
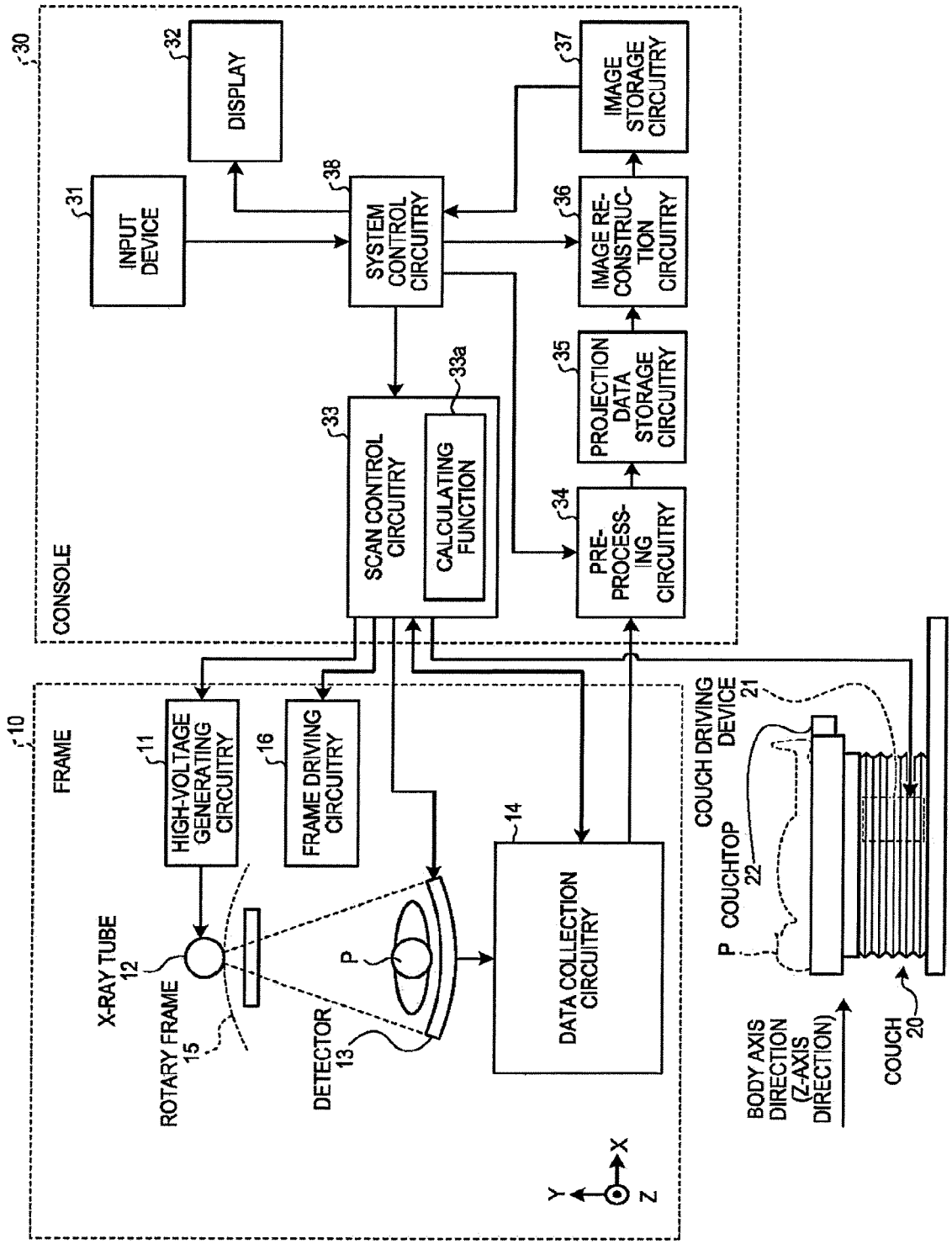
FIG. 1 is a diagram illustrating a configuration example of an X-ray CT apparatus according to a first embodiment.

FIG. 1 is a diagram illustrating a configuration example of an X-ray CT apparatus according to a first embodiment. As illustrated in FIG. 1, the X-ray CT apparatus according to the first embodiment includes a frame 10, a couch 20, and a console 30.

Figure 2:
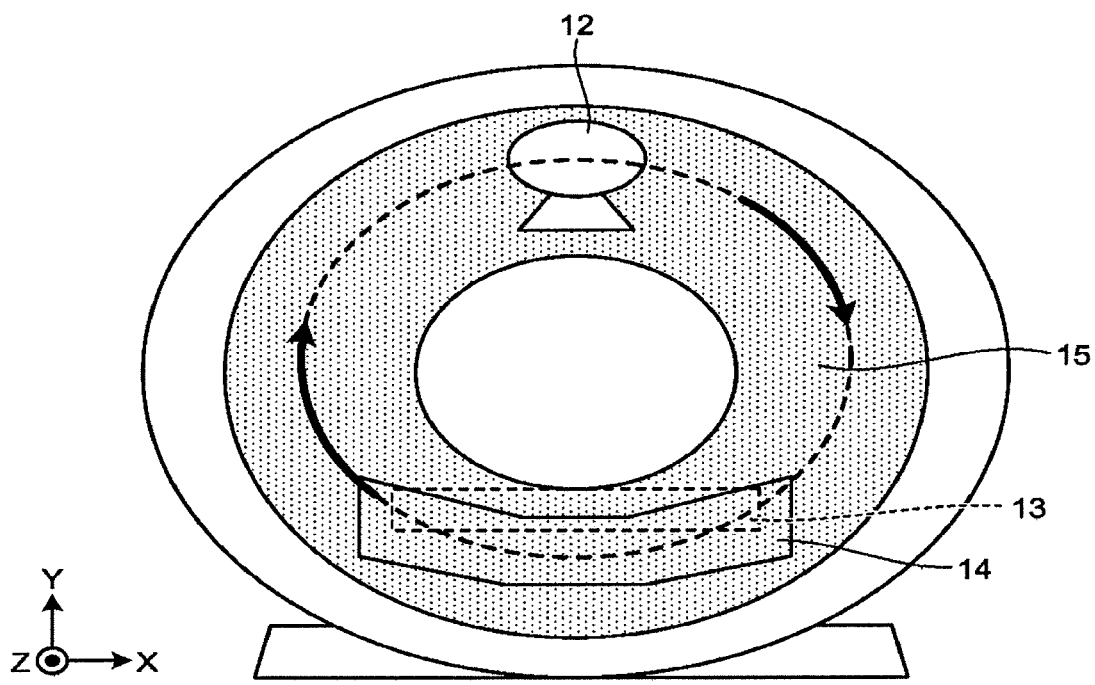
FIG. 2 is a front view of a frame device according to the first embodiment.

The frame 10 is an apparatus applying X-rays to a subject P, and collecting data relating to the X-rays transmitted through the subject P, and includes high-voltage generating circuitry 11, an X-ray tube 12, a detector 13, data collecting circuitry 14, a rotary frame 15, and frame driving circuitry 16. In the frame 10, an orthogonal coordinate system formed of an X axis, a Y axis, and a Z axis is defined, as illustrated in FIG. 1. Specifically, the X axis indicates a horizontal direction, the Y axis indicates a vertical direction, and the Z axis indicates a rotation center axis direction of the rotary frame 15 in a state in which the frame 10 is not tilted. FIG. 2 is a front view of the frame 10 according to the first embodiment.

As illustrated in FIG. 2, the rotary frame 15 is an annular frame supporting the X-ray tube 12 and the detector 13 such that the X-ray tube 12 and the detector 13 are opposed to each other with the subject P interposed therebetween. The rotary frame 15 is rotated at high speed in a circular orbit with the subject P serving as the center by the frame driving circuitry 16, which will be described later.

The X-ray tube 12 is a vacuum tube applying an X-ray beam to the subject P with high voltage supplied from the high-voltage generating circuitry 11, which will be described later. The X-ray tube 12 applies an X-ray beam to the subject P, with rotation of the rotary frame 15.

The high-voltage generating circuitry 11 is electrical circuitry having a function of supplying high voltage to the X-ray tube 12, and the X-ray tube 12 generates X-rays using high voltage supplied from the high-voltage generating circuitry 11. Specifically, the high-voltage generating circuitry 11 adjusts a tube voltage and/or a tube current supplied to the X-ray tube 12, to adjust the X-ray quantity applied to the subject P. The high-voltage generating circuitry 11 receives control from scan control circuitry under the control of system control circuitry 38.

The frame driving circuitry 16 is an electrical circuitry having a function of turning the X-ray tube 12 and the detector 13 on the circular orbit with the subject P serving as the center, by rotating and driving the rotary frame 15. The frame driving circuitry 16 receives control from the scan control circuitry 33, under the control of the system control circuitry 38.

Figure 3:
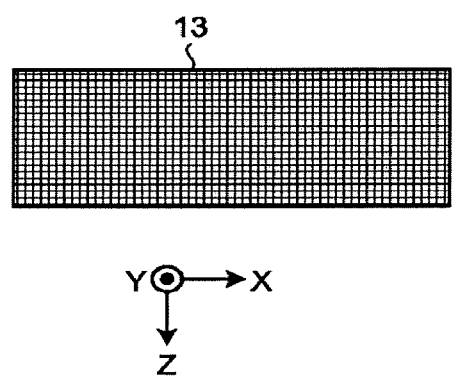
FIG. 3 is a diagram for explaining an example of a detector according to the first embodiment.

The detector 13 is a photon counting detector, and includes a plurality of X-ray detection elements (also referred to as "sensor" or "detection elements") to count light derived from X-rays transmitted through the subject P. As an example, each of the X-ray detection elements included in the detector 13 according to the first embodiment is an indirect-conversion area detector formed of a scintillator and an optical sensor. The optical sensor is, for example, a silicon photomultiplier (SiPM). Each of the X-ray detection elements of the detector 13 outputs an electrical signal (pulse) corresponding to the incident X-ray photon. The electrical signal output from each X-ray detection element is also referred to as detection signal. Specifically, the detector 13 includes a plurality of detection elements each of which detects X-rays and outputs a detection signal. The peak value of the electrical signal (pulse) has correlation with the energy value of the X-ray photon. FIG. 3 is a diagram for explaining an example of the detector 13 according to the first embodiment.

FIG. 3 illustrate an enlarged view the detector 13 illustrated in FIG. 2. FIG. 3 illustrates the detector 13 as viewed from the Y-axis side. As illustrated in FIG. 3, the detector 13 has a structure in which X-ray detection elements are arranged on a surface in a two-dimensional manner. For example, a plurality of lines of x-ray detection elements arranged in the channel direction (X-axis direction in FIG. 3) are arranged along the body axis direction (Z-axis direction in FIG. 3) of the subject P.

With reference to FIG. 2 again, the data collection circuitry 14 is electrical circuitry having a function of collecting a counting result serving as a result of counting processing using the detection signals of the detector 13. The data collection circuitry 14 counts the photons (X-ray photons) derived from the X-rays applied from the X-ray tube 12 and transmitted through the subject P, and collects a result of discriminating the energy of the counted photons as the counting result. The data collection circuitry 14 transmits the counting result to the console 30. The data collection circuitry 14 is also referred to as data acquisition system (DAS).

The couch 20 is a device on which the subject P is placed, and includes a couchtop 22 and a couch driving device 21. The couchtop 22 is a plate on which the subject P is placed. The couch driving device 21 moves the couchtop 22 in the 2-axis direction, to move the subject P into the rotary frame 15. The couch driving device 21 is also capable of moving the couchtop 22 in the X-axis direction.

The frame 10 performs, for example, helical scan in which the rotary frame 15 is rotated while the couchtop 22 is moved, to scan the subject P in a helical manner. As another example, the frame 10 performs conventional scan in which the couchtop 22 is moved into place and after that, the rotary frame 15 is rotated with the position of the subject P fixed to scan the subject P in the circular orbit. The following embodiments illustrate the case where change in relative positions of the frame 10 and the couchtop 22 is achieved by controlling the couchtop 22, but the embodiments are not limited thereto. For example, when the frame 10 is a self-propelled frame, traveling of the frame 10 may be controlled to achieve change in relative positions of the frame 10 and the couchtop 22.

The console 30 is a device receiving operator's operations of the X-ray CT apparatus, and reconstructing X-ray CT image data using the counting result collected with the frame 10. As illustrated in FIG. 1, the console 30 includes an input device 31, a display 32, the scan control circuitry 33, preprocessing circuitry 34, projection data storage circuitry 35, image reconstruction circuitry 36, image storage circuitry 37, and the system control circuitry 38.

The input device 31 includes a mouse and/or a keyboard used by the operator of the X-ray CT apparatus to input various instructions and various settings, and transmits information of the instructions and/or settings received from the operator to the system control circuitry 38. For example, the input device 31 receives reconstruction conditions for reconstructing X-ray CT image data, and/or image processing conditions for X-ray CT image data, front the operator. In addition, for example, the input device 31 receives an instruction to execute calibration of the X-ray detection elements, from the operator. The input device 31 instructs the scan control circuitry 33 to execute reconstruction of X-ray CT image data and execute calibration, via the system control circuitry 38.

The display 32 is a monitor referred to by the operator. The display 32 displays X-ray CT image data for the operator, and displays graphical user interface (GUI) to receive various instructions and/or various settings from the operator through the input device 31, under the control of the system control circuitry 38.

The scan control circuitry 33 is electrical circuitry having a function of controlling operations of the high-voltage generating circuitry 11, the detector 13, the frame driving circuitry 16, the data collection circuitry 14, and the couch driving device 21, to control processing of collecting the counting result in the frame 10, under the control of the system control circuitry 38.

In addition, the scan control circuitry 33 according to the first embodiment executes a calculating function 33a, as illustrated in FIG. 1. The details of the calculating function 33a will be described in detail with reference to FIG. 8 and FIG. 9. For example, the scan control circuitry 33 stores the processing function executed with the calculating function 33a serving as a constituent element of the scan control circuitry 33 illustrated in FIG. 1, in the form of a program executable with a computer. The scan control circuitry 33 is, for example, a processor, and achieves a function corresponding to a read program by reading and executing the program. In other words, the scan control circuitry 33 in a state of reading the program includes the calculating function 33a illustrated in the scan control circuitry 33 of FIG. 1.

The preprocessing circuitry 34 is electrical circuitry having a function of performing correction processing, such as logarithmic transformation, offset correction, sensitivity correction, and beam hardening correction, on the counting result transmitted from the data collection circuitry 14, to generate projection data for each energy discrimination range.

The projection data storage circuitry 35 is, for example, a not AND (NAND) flash memory or a hard disk drive (HDD), and stores projection data generated with the preprocessing circuitry 34. Specifically, the projection data storage circuitry 35 stores projection data to reconstruct X-ray CT image data.

The image reconstruction circuitry 36 is electrical circuitry having a function of reconstructing a CT image on the basis of the detection signal of the detector 13. Specifically, the image reconstruction circuitry 36 performs, for example, back projection processing on the projection data stored in the projection data storage circuitry 35, to reconstruct X-ray CT image data. Examples of the back projection processing include back projection processing using filtered back projection (FBP). The image reconstruction circuitry 36 may perform reconstruction processing by, for example, iterative approximation. The image reconstruction circuitry 36 also performs various types of image processing on the X-ray CT image data, to generate image data. The image reconstruction circuitry 36 stores the reconstructed X-ray CT image data and image data generated by various types of image processing in the image storage circuitry 37.

The projection data generated from the counting result obtained by photon counting CT includes information of energy of X-rays attenuated by being transmitted through the subject P. For this reason, the image reconstruction circuitry 36 is capable of reconstructing, for example, X-ray CT image data of a specific energy component. The image reconstruction circuitry 36 is also capable of reconstructing, for example, pieces of X-ray CT image data for respective energy components.

The image reconstruction circuitry 36 is also capable of assigning tones corresponding to energy components to each of the pixels of the X-ray CT image data of respective image components, to generate image data in which a plurality of pieces of X-ray CT image data colored with different colors corresponding to the respective energy components are superimposed on each other. The image reconstruction circuitry 36 is also capable of generating, for example, image data enabling identification of the substance, using the K absorption edge peculiar to the substance. Examples of other image data generated with the image reconstruction circuitry 36 include monochromatic X-ray image data, density image data, and effective atomic number image data.

The system control circuitry 38 is electrical circuitry having a function of controlling operations of the frame 10, the couch 20, and the console 30, to control the whole X-ray CT apparatus. Specifically, the system control circuitry 38 controls the scan control circuitry 33, to control CT scan performed in the frame 10. The system control circuitry 38 also controls the preprocessing circuitry 34 and the image reconstruction circuitry 36, to control image reconstruction processing and image generation processing in the console 30. The system control circuitry 38 also performs control to display various types of image data stored in the image storage circuitry 37 on the display 32. The image storage circuitry 37 is, for example, a NAND flash memory or an HDD, and stores various types of image data.

The whole configuration of the X-ray CT apparatus according to the first embodiment has been described above. With the structure described above, the X-ray CT apparatus according to the first embodiment reconstructs X-ray CT image data using a photon counting detector.

In photon counting CT, the number of photons are counted, to measure the quantity of the X-rays. The intensity of the X-rays increases with an increase in the number of photons per unit time. Although individual photon have different energies, photon counting CT enables acquisition of information of energy components of the X-rays, by performing photon energy measurement. Specifically, in photon counting CT, data collected by applying X-rays with one type of tube voltage can be divided into a plurality of energy components and imaged. For example, photon counting CT enables acquisition of image data enabling identification of the substance using difference in K absorption edge.

To accurately count photons for respective energies using the photon counting detector 13 having the structure described above, calibration is required for the energy values of photons measured in the detector 13. FIG. 4 to FIG. 7 are diagrams for explaining prior art.

Figure 4:
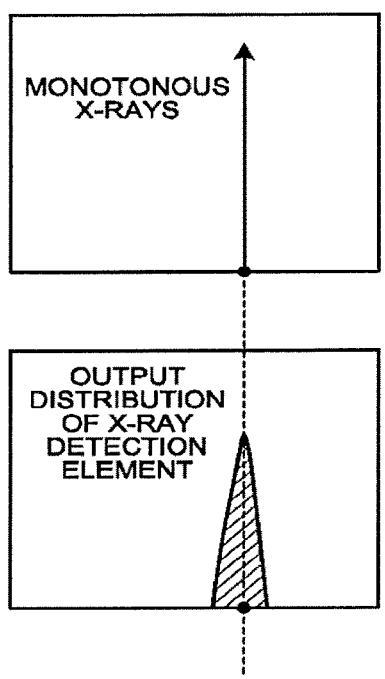
FIG. 4 is a diagram for explaining prior art.

FIG. 4 illustrates a calibration method according to prior art using an X-ray tube capable of applying monochromatic X-rays having a known specific energy. The upper drawing in FIG. 4 illustrates an X-ray spectrum of the X-ray tube, and the lower drawing in FIG. 4 illustrates a spectrum of X-rays detected with the X-ray detection elements. For example, when the X-ray tube 12 included in the X-ray CT apparatus is capable of applying monochromatic X-rays having a known specific energy as illustrated in the upper drawing in FIG. 4, the correlation between the photon detection signal and the energy value can be determined, by detecting the peak of the detection signal of the X-ray photons made incident on the X-ray detection elements as illustrated in the lower drawing in FIG. 4.

Figure 5:
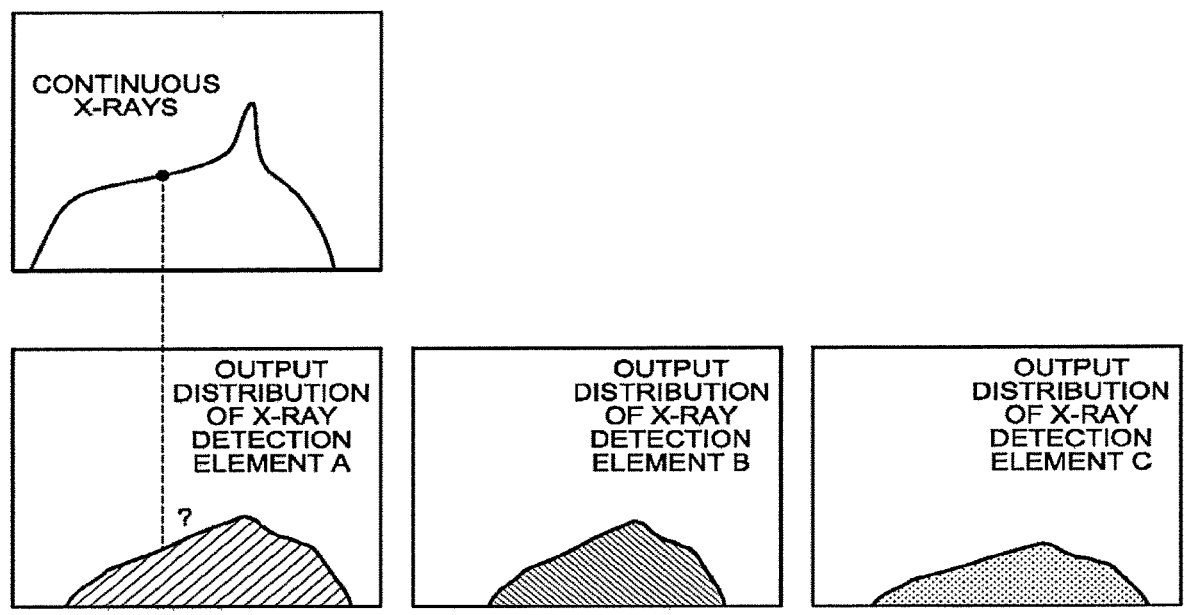
FIG. 5 is a diagram for explaining prior art.

However, the X-ray tube 12 included in the X-ray CT apparatus generally generates continuous X-rays having an energy distribution. For this reason, a calibration method using an X-ray tube capable of applying monochromatic X-rays having a known specific energy is not applicable. FIG. 5 illustrates a calibration method according to prior art using an X-ray tube applying continuous X-rays having an energy distribution. The upper drawing in FIG. 5 illustrates an X-ray spectrum of the X-ray tube, and the lower drawings in FIG. 5 illustrate respective spectra of X-rays detected by the X-ray detection element A to the X-ray detection element C from the left. As illustrated in the upper drawing of FIG. 5, the X-ray tube 12 applies continuous X-rays having an energy distribution. As illustrated in the lower drawings of FIG. 5, each of the spectra of the detection signals of the X-ray photons made incident on the respective X-ray detection elements has a wide energy distribution. As described above, even when continuous X-rays are applied to a photon counting X-ray detector, difficulty exists in detecting the peak of the detection signal of photons with sufficient accuracy, when the energy resolution of the detector 13 is insufficient.

Figure 6:
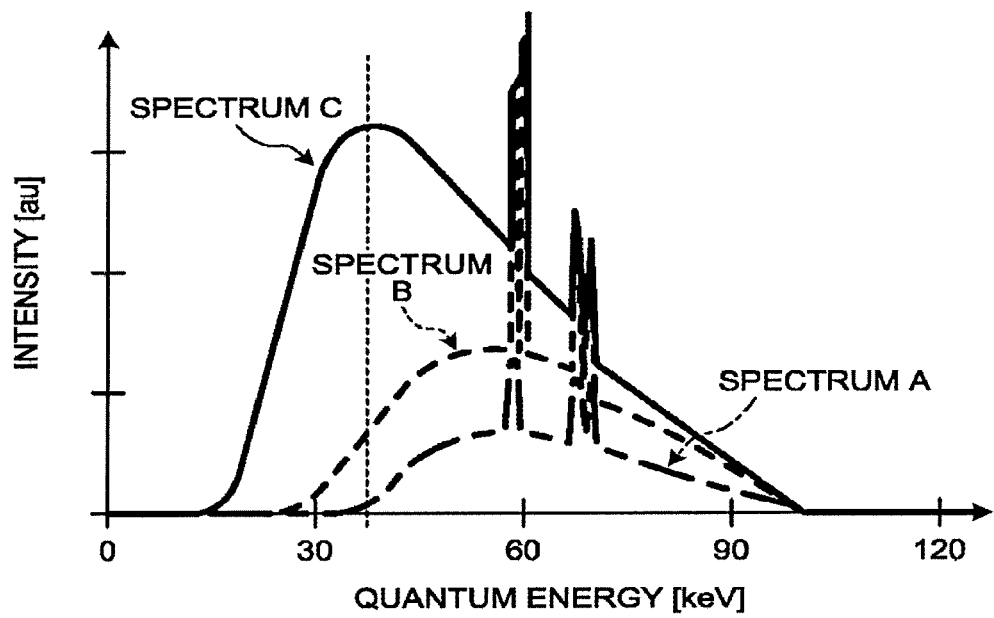
FIG. 6 is a diagram for explaining prior art.

Even when the X-ray tube 12 included in the X-ray CT apparatus generates continuous X-rays, the peak may be calculated, when the output of X-rays is increased. FIG. 6 illustrates three spectra in the case where continuous X-rays are generated under the X-ray application conditions with the same tube voltage and with different tube currents. The example of FIG. 6 illustrates the case where continuous X-rays are generated with the tube current increased gradually in the order of the spectrum A, the spectrum B, and the spectrum C. As illustrated in FIG. 6, in the spectrum C, the peak can be detected, while the peak cannot be detected in the spectrum A or the spectrum B. The horizontal axis in FIG. 6 indicates the energy value, and the vertical axis in FIG. 6 indicates the intensity of X-rays.

Figure 7:
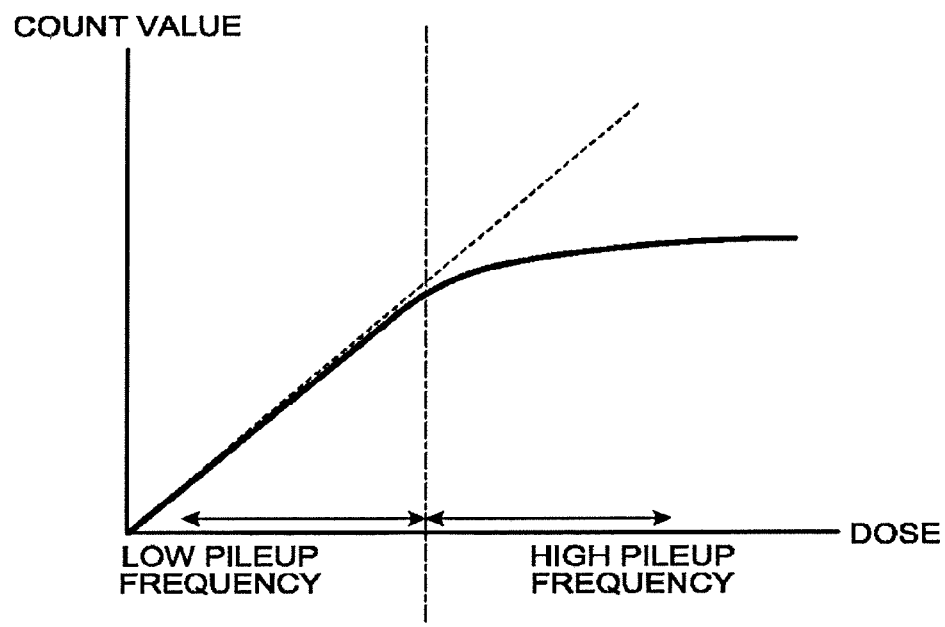
FIG. 7 is a diagram for explaining prior art.

However, selecting the peak with high output increases the frequency of occurrence of pileup. The following is an explanation of relation between the output of X-rays and the frequency of occurrence of pileup, with reference to FIG. 7. The horizontal axis in FIG. 7 illustrates the dose of X-rays, and the vertical axis in FIG. 7 illustrates the count value of detected X-rays. As illustrated with a broken line in FIG. 7, the dose of X-rays is theoretically proportional to the count value of the detected X-rays. Specifically, the count value of X-rays increases in proportion to an increase in the dose of X-rays. However, actually, as illustrated with a solid line in FIG. 7, when the dose of X-rays increases, the count value of X-rays does not increase in proportion to the dose of the X-rays, even when the dose of X-rays increases. Specifically, when the dose is high, the frequency of occurrence of pileup increases, although the peak increases. When the dose is low, the frequency of occurrence of pileup decreases, although the peak decreases.

In addition, when the frequency of occurrence of pileup increases, the accuracy of calibration decreases. Specifically, in calibration, applying X-rays with small dose that does not cause pileup is suitable. However, when the detector 13 has insufficient energy resolution, difficulty occurs in detecting the peak of the detection signals of photons with sufficient accuracy, and the accuracy of calibration decreases.

In nuclear medicine imaging apparatuses, a calibration method is known. In the calibration method, a standard source with a known energy value is disposed on each detection element. When this method is applied to calibration of the area detector of an X-ray CT apparatus, long hours of work is required. For this reason, there is the problem that calibration to calibrate variations of X-ray energy sensitivity of each of X-ray detection elements cannot be accurately and simply performed.

Figure 8:
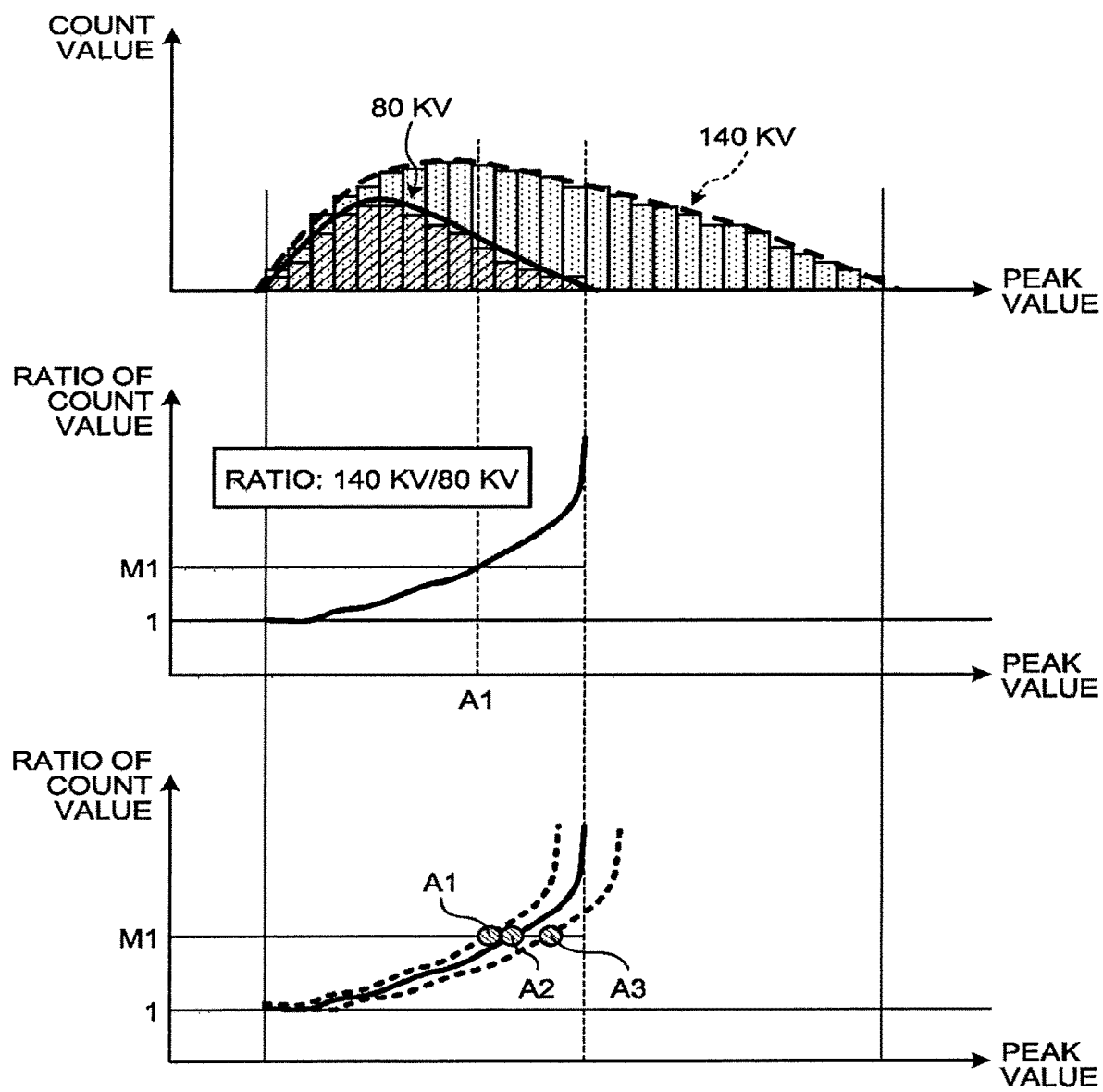
FIG. 8 is a diagram for explaining a processing operation of a calculating function according to the first embodiment.
Figure 9:
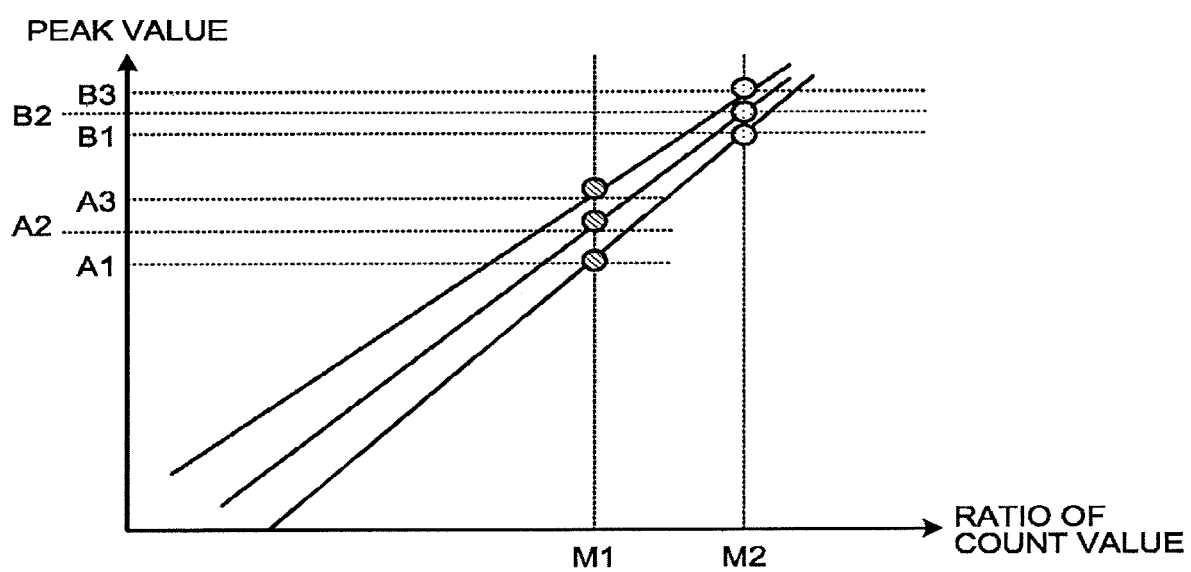
FIG. 9 is a diagram for explaining a processing operation of the calculating function according to the f rat embodiment.
Figure 10:
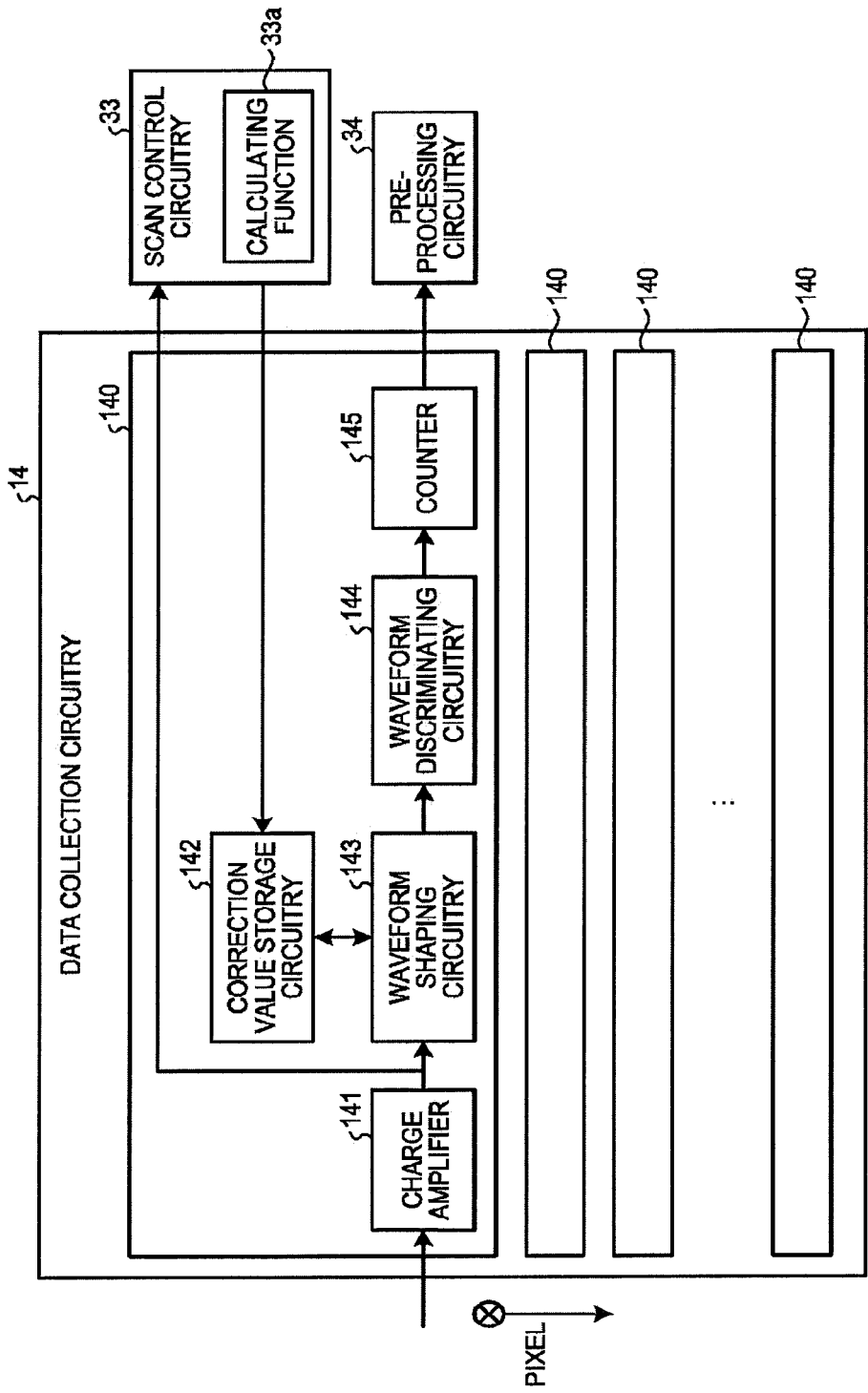
FIG. 10 is a diagram for explaining a configuration example of data collection circuitry according to the first embodiment.

For this reason, to perform calibration accurately and simply, the X-ray CT apparatus according to the first embodiment calibrates a detection signal of each of detection elements using a correction value based on a result of arithmetic processing using a plurality of signals output from detection elements included in a photon counting X-ray detector under a plurality of X-ray application conditions, each of the detection elements detecting X-rays and outputting a detection signal and included in the photon counting detector. For example, the X-ray T apparatus according to the first embodiment specifies a feature point on the basis of a result of arithmetic processing using a plurality of signals, and calculates a correction value using the feature point. In addition, the X-ray CT apparatus according to the first embodiment generates an image using the calibrated detection signals of the detection elements. The correction value calculating function of the X-ray CT apparatus as described above is achieved with a calculating function 33a, and the data collection circuitry 14 achieves a function of calibrating a detection signal of each of the detection elements of the X-ray CT apparatus. The following is a detailed explanation of the data collection circuitry 14 and the calculating function 33a according to the first embodiment with reference to FIG. 8 to FIG. 10. FIG. 8 and FIG. 9 are diagrams for explaining a processing operation of the calculating function 33a according to the first embodiment, and FIG. 10 is a diagram illustrating a configuration example of the data collection circuitry 14 according to the first embodiment.

First, the following is an explanation of processing of calculating a correction value with the calculating function 33a. The upper drawing in FIG. 8 illustrates the case where X-rays are applied under two X-ray application conditions in which the same tube current is used and different tube voltages of 80 KV and 140 KV are used, as a plurality of X-ray application conditions. The upper drawing of FIG. 8 also illustrates an example of X-ray spectra detected with the detection elements included in the photon counting detector 13, in the case where X-rays are applied under the two X-ray application conditions. The horizontal axis in the upper drawing of FIG. 8 indicates the peak value of photons detected with the detection elements, and the vertical axis in the upper drawing of FIG. 8 indicates the count value of photons detected with the detection elements. The example illustrated in the upper drawing of FIG. 8 illustrates, for example, X-ray spectra detected in the case where X-rays are applied under the two X-ray application conditions in which the same tube current is used and different tube voltages of 80 KV and 140 KV are used. In the explanation, for convenience of explanation, the X-ray spectrum of 140 KV is referred to as first signal, and the X-ray spectrum of 20 KV is referred to as second signal. The X-ray application conditions are different in at least one of the tube voltage and the tube current. When the tube voltage and the tube current are adjusted as X-ray application conditions, they are desirably adjusted to have an X-ray dose that decreases the frequency of occurrence of pileup.

The calculating function 33a specifies a feature point on the basis of a result of arithmetic processing using a plurality of signals, and calculates a correction value using the feature point. For example, the calculating function 33a calculates a ratio of the count value of the first signal to the count value of the second signal, in the signals. The middle drawing in FIG. 8 is a graph plotting the ratio of the count value of the first signal to the count value of the second signal at the same peak value for the first signal and the second signal detected in the detection element. A in the detection elements included in the detector 13.

The calculating function 33a specifies the peak value at which the ratio of the count value of the first signal and the count value of the second signal has a predetermined value, as the feature point. The feature point is a uniquely determined value. For this reason, the calculating function 33a specifies a feature point, for example, from the peak value of a period in which a plurality of signals monotonously increase or monotonously decrease. More specifically, the calculating function 33a specifies a feature point from the peak value at which the change quantity of the count value of one of the signals becomes maximum. In the example illustrated in the middle drawing of FIG. 8, the calculating function 33*a* specifies the peak value A1 at which the ratio of the count values is M1, as the feature point.

The calculating function 33*a* also specifies, as the feature point, the peak value at which the ratio of the count value of the first signal to the count value of the second signal is M1, for each of the detection elements other than the detection element A in the same manner. The lower drawing in FIG. 8 is a graph plotting the ratio of the count value of the first signal to the count value of the second signal at the same peak value for each peak value for the first signal and the second signal detected in the detection element A, the detection element B, and the detection element C. The calculating function 33*a* specifies the peak value at which the ratio of the count values is M1, as the feature point. In the example of the lower drawing in FIG. 8, the feature point of the detection element A is indicated with peak value A1, the feature point of the detection element B is indicated with peak value A2, and the feature point of the detection element C is indicated with peak value A3. As described above, the calculating function 33*a* specifies, as the feature point, the peak value among the signals at which the ratio of the count value of the first signal to the count value of the second signal has a predetermined value. In other words, when X-rays are applied under two X-ray application conditions in which the tube current is the same and different tube voltages of 80 KV and 140 KV are used, the calculating function 33*a* specifies a feature point of each of the detection elements. For convenience of explanation, the two X-ray application conditions in which the tube current is the same and different tube voltages of 80 KV and 140 KV are used is referred to as first application condition, and the feature point specified under the first application condition is referred to as first feature point. The first application condition is an example of the first X-ray application condition.

Thereafter, the calculating function 33*a* also specifies a feature point under a second application condition, which is different from the first application condition, in the same manner. The second application condition is an example of the second X-ray application condition. It suffices that the second application condition includes X-ray application conditions in which at least one of the X-ray application conditions included in the first application condition is different. In other words, in the second application condition, at least one out of the tube voltage and the tube current is different from the X-ray application condition included in the first application condition. For example, in the second application condition, the tube current may be the same as that of the first application condition and the tube voltage may be 100 KV and 140 KV, or the tube voltage may be 60 KV and 100 KV, as the X-ray application condition different from the X-ray application conditions included in the first application condition. As another example, in the second application condition, the tube voltage may be the same as that of the first application condition, and the tube current may be set different from the first application condition. As another example, in the second application condition, both the tube current and the tube voltage may be set different from those of the first application condition. The feature point specified under the second application condition is referred to as the second feature point.

The calculating function 33*a* specifies, for example, the peak value at which the ratio of the count value of the first signal to the count value of the second signal has a predetermined value in the second application condition, as the feature point. For example, the calculating function 33*a* specifies the peak value at which the ratio of the count values is M2, as the feature point. As an example, the calculating function 33*a* specifies the second feature point of the detection element A as the peak value B1, the second feature point of the detection element B as the peak value B2, and the second feature point of the detection element C as the peak value B3.

When the peak value specified under the first application condition is close to the peak value specified under the second application condition, accuracy of calibration decreases. For this reason, the first application condition and the second application condition are desirably set such that the peak value specified under the first application condition is not close to the peak value specified under the second application condition.

Thereafter, the calculating function 33*a* calculates a correction value by linear regression using the first feature point specified from the first signal and the second signal of the first application condition, and the second feature point specified from the first signal and the second signal of the second application condition. FIG. 9 illustrates processing of calculating a correction value performed with the calculating function 33*a* using linear regression.

The horizontal axis of FIG. 9 illustrates the ratio of the count values, and the vertical axis of FIG. 9 illustrates the peak value. In the example illustrated in FIG. 9, the first feature point of the detection element A in the first application condition is set as the peak value A1, and the second feature point of the detection element A in the second application condition is set as the peak value B1. Also in the example illustrated in FIG. 9, the first feature point of the detection element B in the first application condition is set as the peak value A2, and the second feature point of the detection element B in the second application condition is set as the peak value B2. Also in the example illustrated in FIG. 9, the first feature point of the detection element C in the first application condition is set as the peak value A3, and the second feature point of the detection element C in the second application condition is set as the peak value B3.

The energy and the peak value have linear relation. For example, suppose that the peak value is An, the energy is En, the gain is $\alpha$, and the offset is $\beta$, then the relation "An=$\alpha$En+$\beta$" is satisfied. For this reason, the calculating function 33*a* calculates the gain ($\alpha$) and the offset ($\beta$) of each of the detection elements, by plotting the ratio of the peak value to the count value as illustrated in FIG. 9. In such a case, the energy value in the case where the ratio of the count values is M1 and the energy value in the case where the ratio of the count values is M2 are set in advance. For example, the calculating function 33*a* determines the energy value of the first feature point and the energy value of the second feature point using X-ray spectra derived in advance for the respective X-ray application conditions, to calculate the correction value. As an example, the energy values for M1 and M2 are analytically determined with a model of the tube voltage and the X-ray spectrum. More specifically, the energy value with which the ratio of the count values is M1 and the energy value with which the ratio of the count values is M2 are determined using X-ray spectra derived in advance for the respective tube voltages. The embodiment illustrates an example in which X-ray spectra are derived in advance for the respective tube voltages, but X-ray spectra in which the tube current is further changed in the respective tube voltages may be derived in advance. As another example, the energy values for M1 and M2 may be measured in advance with a detector with high energy resolution, such as a Ge detector, as described later with reference to FIG. 16. The calculating function 33a calculates the gain (α) and the offset (β) calculated for each detection element as correction value, in correction value storage circuitry 142 described later.

The following is an explanation of the data collection circuitry 14 with reference to FIG. 10. As illustrated in FIG. 10, the data collection circuitry 14 includes a plurality of collection units 140. The collection units 140 correspond to the respective X-ray detection elements. Accordingly, the number of collection units 140 provided is equal to the number of the X-ray detection elements. Each of the collection units 140 includes a charge amplifier 141, correction value storage circuitry 142, waveform shaping circuitry 143, waveform discriminating circuitry 144, and a counter 145.

The correction value storage circuitry 142 is, for example, a read only memory (ROM), a NAND flash memory, or an HDD, and stores detection signals of the X-ray detection element, and a correlation value for calibration. The correction value is calculated with the calculating function 33a included in the scan control circuitry 33.

The charge amplifier 141 is electrical circuitry having a function of integrating and amplifying a charge collected in response to the photon made incident on the X-ray detection element, and outputting the charge as a pulse signal of the electric quantity. More specifically, the charge amplifier 141 is electrical circuitry having an amplifying function. The pulse signal output from the charge amplifier 141 has a wave height and an area corresponding to the energy quantity of the photon.

The output side of the charge amplifier 141 is connected with the waveform shaping circuitry 143 and the scan control circuitry 33. The charge amplifier 141 switches the output of the pulse signal to one of the scan control circuitry 33 and the waveform shaping circuitry 143, in accordance with the instruction of the scan control circuitry 33. For example, in the case of performing processing of calculating a correction value for calibration, the charge amplifier 141 outputs the pulse signal to the calculating function 33a of the scan control circuitry 3. In this manner, the calculating function 33a calculates a correction value. By contrast, when the X-ray CT image data is reconstructed, the charge amplifier 141 outputs the pulse signal to the waveform shaping circuitry 143.

The waveform shaping circuitry 143 is electrical circuitry having a function of calibrating a detection signal of each of the detection elements using a correction value calculated from a plurality of signals output from the detection elements and corresponding to respective X-ray application conditions relating to continuous X-rays. For example, the waveform shaping circuitry 143 calibrates the detection signal of the detection element using the correction value based on a result of arithmetic processing using a plurality of signals output from the detection element with X-ray application conditions. In other words, the waveform shaping circuitry 143 calculates a feature point in the energy spectrum on the basis of count values of a plurality of signals, and calculates a correction value on the basis of the feature point. For example, the waveform shaping circuitry 143 calibrates the detection signal detected with the photon counting detector 13 for each X-ray detection element, on the basis of the correction value calculated for the X-ray detection element. More specifically, the waveform shaping circuitry 143 adjusts the frequency characteristic of the pulse signal output from the charge amplifier 141, and supplies the gain and the offset to shape the waveform of the pulse signal. The output side of the waveform shaping circuitry 143 is connected with the waveform discriminating circuitry 144.

The waveform discriminating circuitry 144 is electrical circuitry having a function of comparing the wave height or the area of the response pulse signal for the incident photon with preset thresholds corresponding to a plurality of energy bands to be discriminated, and outputting a result of comparison with the thresholds to the following counter 145.

The counter 145 is electrical circuitry having a function of counting a discrimination result of the waveform of the response pulse signals for each of the corresponding energy bands, and outputting a photon counting result as digital data to the preprocessing circuitry 34 of the console 30. More specifically, the counter 145 is, for example, digital circuitry processing numerical values by counting clock pulses.

Specifically, the counter 145 collects the incident positions (detection position) of the X-ray photons counted by discriminating the pulses output from the X-ray detection element, and the energy values of the X-ray photons, as the counting result, for each phase (tube bulb phase) of the X-ray tube 12. The counter 145 collects, for example, the position of the X-ray detection element outputting the pulse used for counting, as the incident position.

For example, the counting result collected with the counter 145 is information such as "the count value of photons with the energy discrimination area "E1<E≤E2" is "N1", and the count value of photon with the energy discrimination area "E2<≤E3" is "N2", in the X-ray detection element in the incident position "P11" at the tube bulb phase "α1"". As another example, the counting result collected with the counter 145 is information such as "the count value of photons per unit time with the energy discrimination area "E1<E≤E2" is "n1", and the count value of photon per unit time with the energy discrimination area "E2<E≤E3" is "n2", in the X-ray detection element in the incident position "P11" at the tube bulb phase "α1"".

As described above, a counting result corresponding to a plurality of energy bands is output from the X-ray detection element corresponding to one pixel of the detector 13, as X-ray detection data, to the preprocessing circuitry 34. As a result, the image reconstruction circuitry 36 generates an image using calibrated detection signals of the detection elements.

Figure 11:
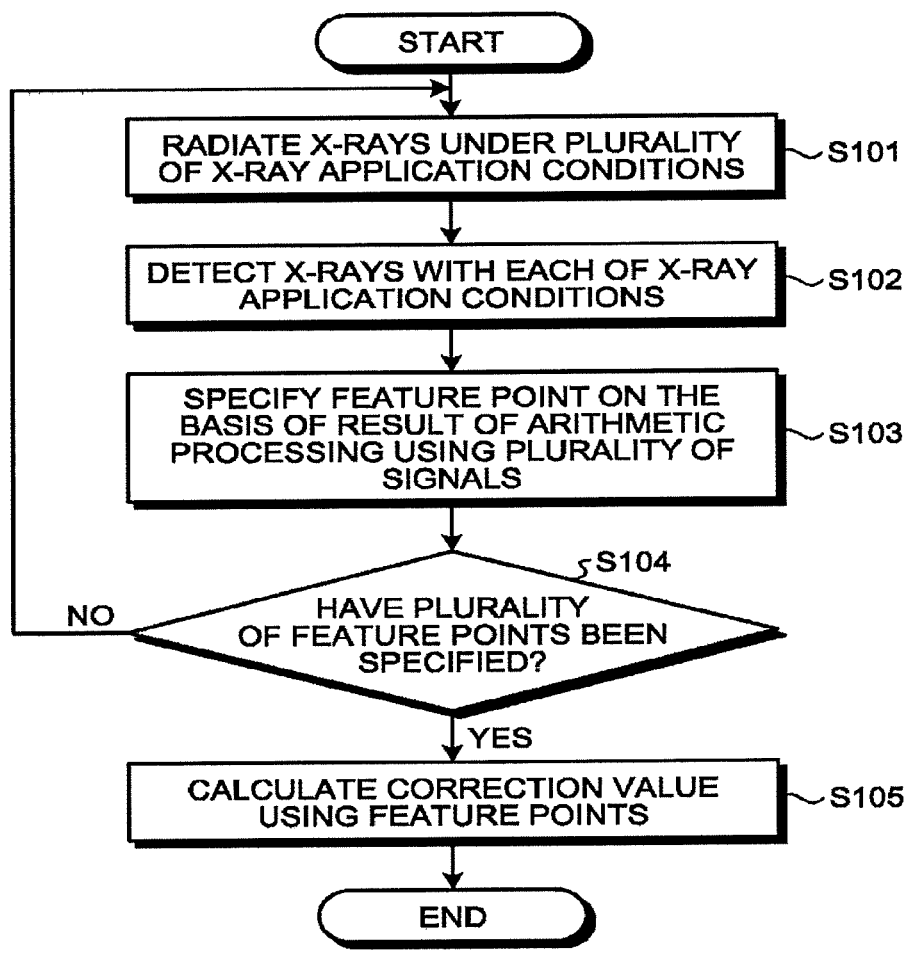
FIG. 11 is a flowchart illustrating a process of processing of calculating a correction value performed by the X-ray CT apparatus according to the first embodiment.

FIG. 11 is a flowchart illustrating a process of processing of calculating a correction value performed with the X-ray CT apparatus according to the first embodiment. Step S101 is a step achieved with the scan control circuitry 33. At Step S101, the scan control circuitry 33 controls the X-ray tube 12 to cause the X-ray tube 12 to radiate X-rays under a plurality of X-ray application conditions. For example, the scan control circuitry 33 applies X-rays under two X-ray application conditions with different tube voltages of 80 KV and 140 KV, as the first application condition.

Step S102 is a step achieved with the detector 13. At Step S102, the detector 13 detects X-rays with each of the X-ray application conditions. For example, as the first application condition, the detector 13 detects X-rays applied with the X-ray application condition with the tube voltage of 140 KV as the first signal, and detects X-rays applied with the X-ray application condition with the tube voltage of 80 KV as the second signal.

Step S103 to Step S105 are steps corresponding to the calculating function 33a. The calculating function 33a is achieved by the scan control circuitry 33 reading and executing a predetermined program stored in the scan control circuitry 33. At step S103, the calculating function 33a specifies the feature point, on the basis of a result of arithmetic processing using a plurality of signals. For example, the calculating function 33a calculates the ratio of the count value of the first signal to the count value of the second signal among a plurality of signals, and specifies the peak value at which the calculated ratio has a predetermined value, as the feature point.

At Step S104, the calculating function 33a determines whether a plurality of feature points have been specified for each detection element. When it is determined that a plurality of feature points have been specified for each detection element (Yes at Step S104), the calculating function 33a proceeds to Step S105. For example, the calculating function 33a determines that the peak value in the case where the ratio of the count values is M1 and the peak value in the case where the ratio of the count values is M2 are specified, and proceeds to Step S105. By contrast, when it is determined that a plurality of feature points have not been specified for each detection element (No at Step S104), the calculating function 33a proceeds to Step S101. In such a case, for example, the scan control circuitry 33 causes radiation of X-rays under the second application condition different from the first application condition.

At Step S105, the calculating function 33a calculates a correction value using a plurality of feature points for each X-ray detection element. In such a case, the energy value in the case where the ratio of the count values is M1 and the peak value in the case where the ratio of the count values is M2 are set in advance. In addition, for example, the calculating function 33a calculates the gain ($\alpha$) and the offset ($\beta$) as correction value for each detection element by linear regression using the peak value and the energy in the case where the ratio of the court values is M1 and the peak value and the energy in the case where the ratio of the count values is M2. The calculating function 33a stores the correction value calculated for each of the X-ray detection element in the correction value storage circuitry 142 in the collection unit 140 corresponding to the X-ray detection element.

Figure 12:
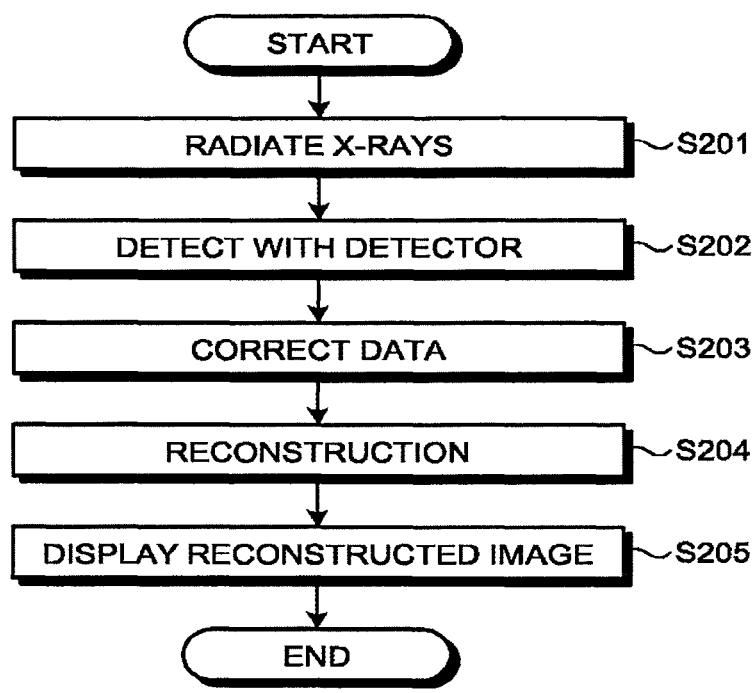
FIG. 12 is a flowchart illustrating a process of processing of reconstructing an X-ray CT image performed by the X-ray CT apparatus according to the first embodiment.

FIG. 12 is a flowchart illustrating a process of processing of reconstructing an X-ray CT image performed with the X-ray CT apparatus according to the first embodiment. Step S201 is a step achieved with the scan control circuitry 33. At Step S201, the scan control circuitry 33 controls the X-ray tube 12 to cause the X-ray tube 12 to radiate X-rays. Step S202 is a step achieved with the detector 13. At Step S202, each of the X-ray detection elements of the detector 13 detects X-rays. Step S203 is a step achieved with the waveform shaping circuitry 143 of the data collection circuitry 14. At Step S203, the waveform shaping circuitry 143 calibrates the detection signal detected with the photon counting detector 13 for each X-ray detection element on the basis of the correction value.

Step S204 is a step achieved with the image reconstruction circuitry 36. At Step S204, the image reconstruction circuitry 36 reconstructs X-ray CT image data on the basis of the calibration detection signal. Step S205 is a step achieved with the system control circuitry 38. At Step S205, the system control circuitry 38 displays the reconstructed X-ray CT image on the display 32.

As described above, in the first embodiment, the detection signal of each of the detection elements is calibrated using the correction value based on a result of arithmetic processing using a plurality of signals output from each of the detection elements with a plurality of X-ray application conditions. In this manner, the first embodiment achieves easy calibration.

In addition, in the first embodiment, the detection signal is calibrated without detecting the peak of the detection signal of each of the detection elements. This structure enables calibration of each of the detection elements with sufficient accuracy, even when continuous X-rays are applied to the X-ray detection elements, each of which is formed of a SiPM and a scintillator having resolution lower than that of the direct-conversion detection element.

In addition, in the first embodiment, the correction value is calculated on the basis of a result of arithmetic processing using a plurality of signals obtained by applying X-rays with X-ray application conditions with low pileup frequency. This structure removes influence of pileup, and achieves more accurate calibration.

In addition, because calibration can be achieved easily and accurately even when the detector 13 has a wide area and the number of X-ray detection elements is large, the first embodiment enables a significant reduction in the number of steps of the calibration work in comparison with the calibration method according to prior art.

In addition, according to the first embodiment, calibration is possible by using the energy values measured in advance in feature points, in the standard structure of the existing X-ray CT apparatus. This structure enables easy execution of periodical calibration, and enables stable generation of stable X-ray CT image data with accuracy. As described above, the first embodiment enables provision of a calibration method with simplicity and accuracy.

In addition, the calculating function 33a may perform detection of an X-ray signal with the X-ray detection element of the detector 13 a plurality of times, to minimize the measurement error of the peak value in the feature point. This structure enables the calculating function 33a to enhance the accuracy of the correction value calculated for each of the X-ray detection elements.

Modification of First Embodiment

The first embodiment described above illustrates the case where the calculating function 33a specifies the feature point using the ratio of the count value of the first signal to the count value of the second signal, but the present embodiment is not limited thereto. For example, the calculating function 33a may calculate the correction value by specifying the feature point using a difference between the count value of the first signal to the count value of the second signal.

For this reason, the modification of the first embodiment illustrates the case where the calculating function 33a specifies the feature point using a difference between the count value of the first signal to the count value of the second signal, to calculate the correction value. In the modification of the first embodiment, the spectrum is modified by using a filter to further emphasize the difference in spectrum, and the difference in spectrum is further emphasized to emphasize the feature point to be calibrated, and enhance the accuracy of calibration. FIG. 13 to FIG. 16 are diagrams for explaining the modification of the first embodiment.

Figure 13:
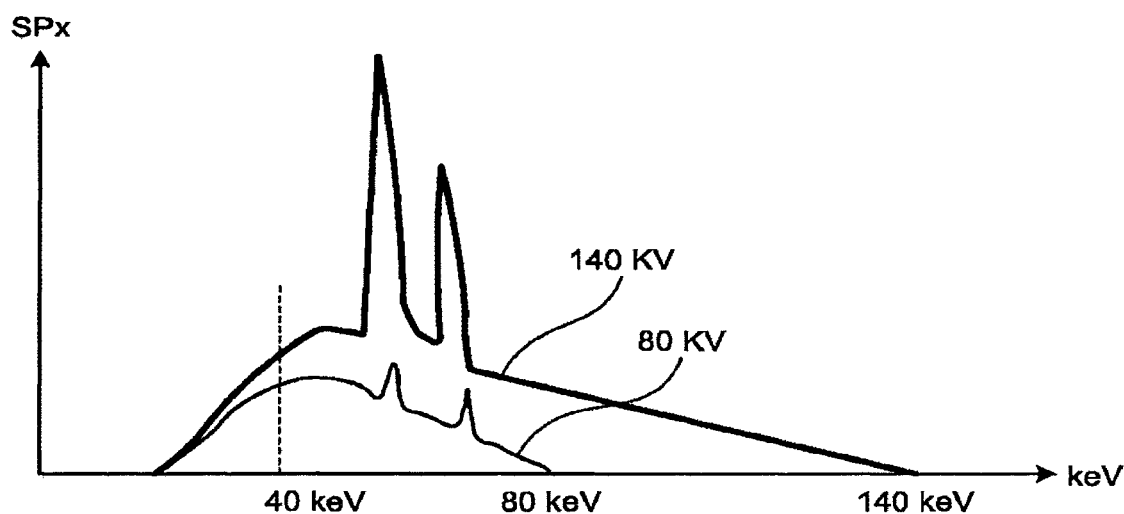
FIG. 13 is a diagram for explaining a modification of the first embodiment.

When the tube voltage is simply changed from 80 KV to 140 KV, the X-ray spectrum of the tube voltage 140 KV also includes X-ray components with low X-ray energy. For example, as illustrated in FIG. 13, the X-ray spectrum of the tube voltage 140 KV also includes the X-ray spectrum of the tube voltage 80 KV. This structure relatively reduces the difference in X-ray absorption coefficient of the substance in the subject between the X-ray projection data with the tube voltage 140 KV and the tube voltage 80 KV, and is not suitable for calibration using the difference in absorption coefficient caused by the difference in tube voltage.

Figure 14:
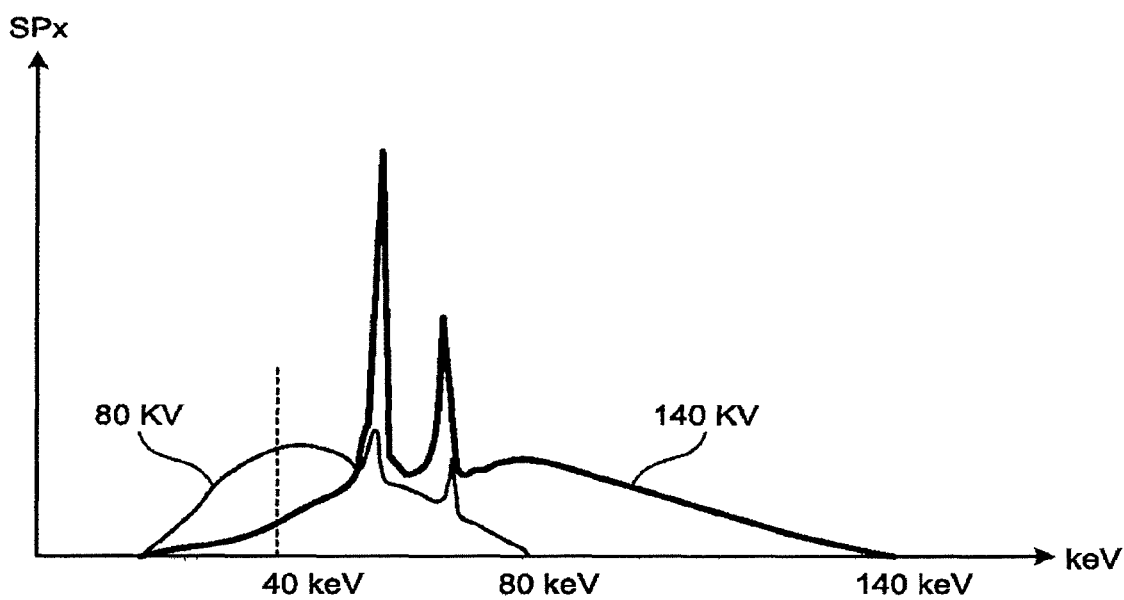
FIG. 14 is a diagram for explaining a modification of the first embodiment.

For this reason, when the tube voltage is changed to 140 KV to apply X-rays, a filter is provided to remove X-ray components with low X-ray energy. Specifically, X-ray components with low X-ray energy are removed from the X-ray spectrum with the tube voltage 140 KV. The filter removes X-rays including the peak value at which the first signal has a peak as the predetermined band. For example, as illustrated in FIG. 14, the filter is designed such that the absorption coefficient around the value of the peak (40 keV) of the X-ray spectrum of 80 KV is reversed from that of the cart of the other energy. In the X-ray spectrum with the tube voltage of 80 KV collected in this state, the count number of the peak value corresponding to 40 keV is higher than the count number of the beak values in the X-ray spectrum with the tube voltage of 140 KV. As described above, in the modification of the first embodiment, one X-ray spectrum is modified by using a filter, to further emphasize the difference in spectrum, and execute the processing of calculating the correction value. The following is an explanation of a processing operation of the calculating function 33a according to the modification of the first embodiment, with reference to FIG. 15 and FIG. 16.

Figure 15:
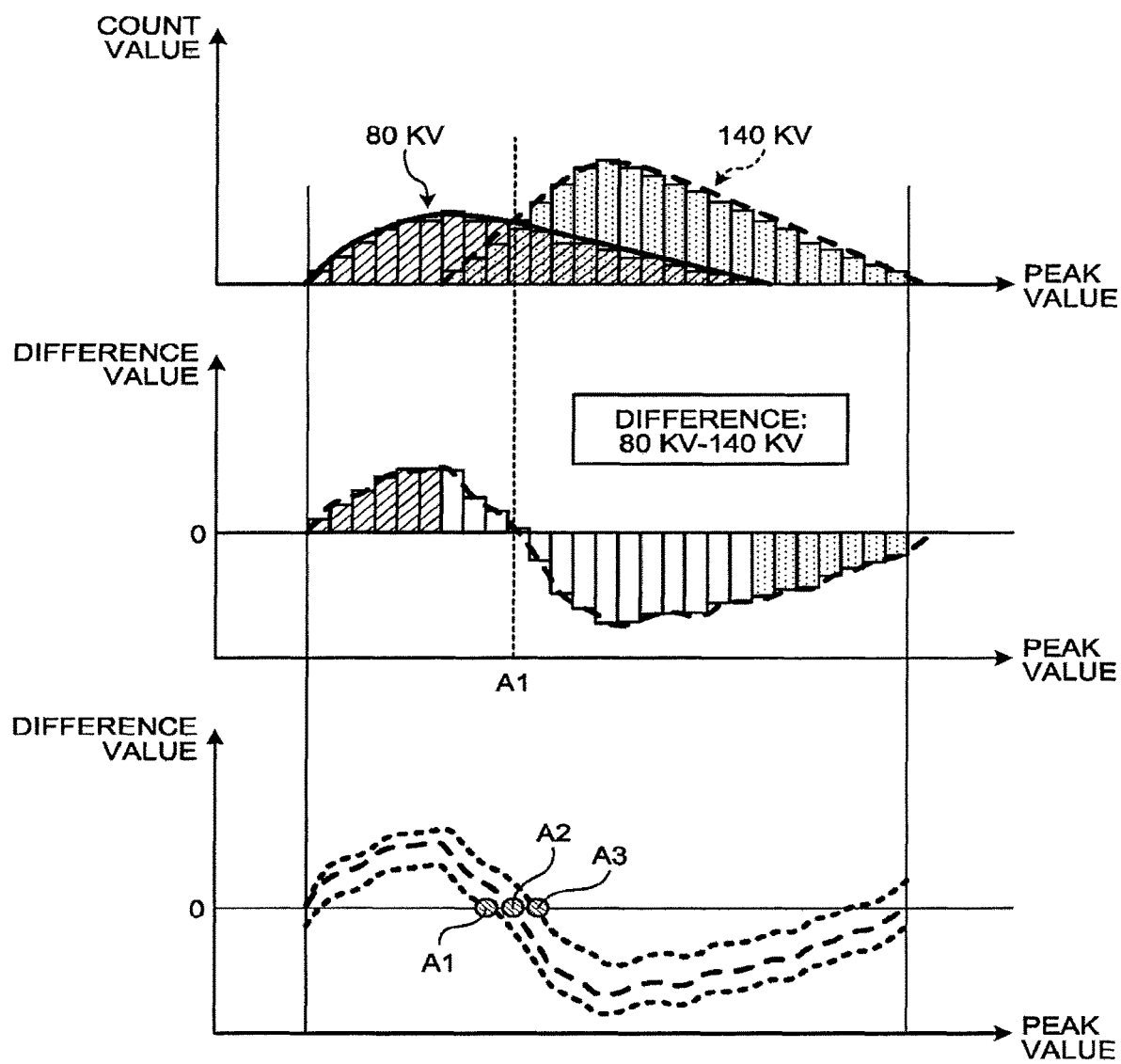
FIG. 15 a diagram for explaining a modification of the first embodiment.

The upper drawing in FIG. 15 illustrates ray spectra detected with the photon counting detector 13, when X-rays are applied under two X-ray application conditions with the same tube current and different tube voltages of 80 KV and 140 KV. The horizontal axis in the upper drawing of FIG. 15 indicates the peak value, and the vertical axis in the upper drawing of FIG. 15 indicates the count value. The example illustrated in the upper drawing of FIG. 15 illustrates the case where X-ray spectrum is detected using a filter removing X-ray components with low X-ray energy from the X-ray spectrum with the tube voltage of 140 KV, when X-rays are applied with the tube voltage of 140 KV. For convenience of explanation, the X-ray spectrum of 140 KV from which X-ray components with low X-ray energy are removed is referred to as the first signal, and the X-ray spectrum of 80 KV is referred to as the second signal. The X-ray application conditions are different from each other in at least one of the tube voltage and the tube current. When the tube voltage and the tube current are adjusted as the X-ray application conditions, it is desirable to adjust them to set X-ray quantity decreasing the frequency of occurrence of pileup.

The calculating function 33a specifies a feature point on the basis of a result of arithmetic processing using a plurality of signals, and calculates the correction value using the feature point. For example, the calculating function 33a calculates a difference value between the count value of the first signal collected under existence of a filter removing X-rays of a predetermined band, and the count value of the second signal collected under absence of the filter among a plurality of signals. The middle drawing in FIG. 15 is a graph plotting a difference value obtained by subtracting the count value of the first signal from the count value of the second signal at the same peak value, for each of the peak values, with respect to the first signal and the second signal detected in the detection element A among the detection elements included in the detector 13.

In addition, the calculating function 33a specifies the peak value among a plurality of signals at which the count value of the first signal collected under existence of the filter removing X-rays of predetermined band is equal to the count value of the second signal collected under absence of the filter, as the feature point. In the example illustrated in the middle drawing of FIG. 15, the calculating function 33a specifies the peak value A1 at which the difference value is 0, as the feature point.

The calculating function 33a also specifies the peak value at which the difference value between the count value of the first signal and the count value of the second signal is 0 as the feature point, for the detection elements other than the detection element A. The lower drawing in FIG. 15 is a graph plotting a difference value between the count value of the first signal and the count value of the second signal at the same peak value, for each of the peak values, with respect to the first signal and the second signal detected in the detection element A, the detection element B, and the detection element C. The calculating function 33a specifies the peak value at which the difference value is C as the feature point. In the example in the lower drawing in FIG. 15, the feature point of the detection element A is indicated with the peak value A1, the feature point of the detection element B is indicated with the peak value A2, and the feature point of the detection element C is indicated with the peak value A3. As described above, the calculating function 33a specifies the peak value among a plurality of signals at which the count value of the first signal collected under existence of a filter removing X-rays of predetermined band is equal to the count value of the second signal collected under absence of the filter, as the feature point. In other words, the calculating function specifies the feature point of each of the detection elements, when X-rays are applied under two X-ray application conditions with the same tube current and different tube voltages of 80 KV and 140 KV. For convenience of explanation, the two X-ray application conditions with the same tube current and different tube voltages of 80 KV and 140 KV is referred to as first application condition, and the feature point specified under the first application condition is referred to as first feature point.

Thereafter, the calculating function 33a specifies the feature point in the same manner, also under the second application condition different from the first application condition. It suffices that the second application condition includes X-ray application conditions in which at least one of the X-ray application conditions included in the first application condition is different. For example, in the second application condition, the tube current may be the same as that of the first application condition and the tube voltage may be 100 KV and 140 KV, or the tube voltage may be 60 KV and 100 KV, as the X-ray application condition different from the X-ray application conditions included in the first application condition. As another example, in the second application condition, the tube voltage may be the same as that of the first application condition, and the tube current may be set different front the first application condition. As another example, in the second application condition, both the tube current and the tube voltage may be set different from those of the first application condition. The feature point specified under the second application condition is referred to as second feature point.

When the peak value specified under the first application condition is close to the peak value specified under the second application condition, accuracy of calibration decreases. For this reason, the first application condition and the second application condition are desirably set such that the peak value specified under the first application condition is not close to the peak value specified under the second application condition.

The calculating function 33a specifies, for example, the peak value at which a difference value between the count value of the first signal and the count value of the second signal in the second application condition is 0, as the feature point. For convenience of explanation, the feature point specified under the second application condition is referred to as second feature point. As an example, the calculating function 33a specifies the second feature point of the detection element A as the peak value B1, the second feature point of the detection element B as the peak value B2, and the second feature point of the detection element C as the peak value B3.

Figure 16:
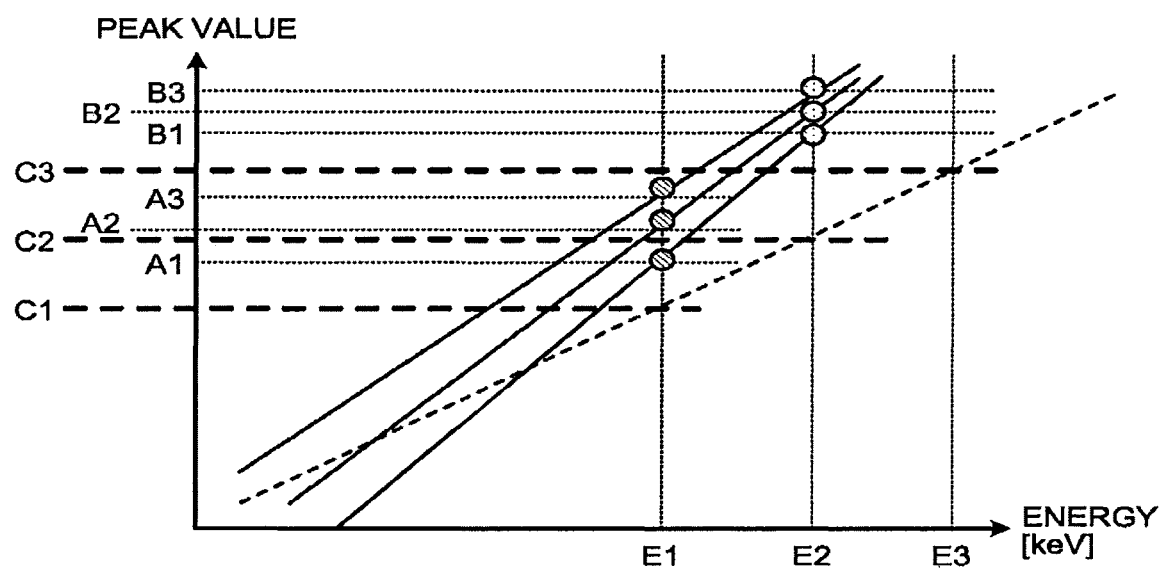
FIG. 16 a diagram for explaining a modification of the first embodiment.

The calculating function 33a specifies the correction value by linear regression using the first feature point specified from the first signal and the second signal of the first application condition, and the second feature point specified from the first signal and the second signal of the second application condition. FIG. 16 illustrates processing of calculating a correction value performed with the calculating function 33a using linear regression. FIG. 16 illustrates the case where the detector with high energy resolution such as a GE detector measures in advance the energy value with a difference value of 0 in the first application condition and the energy value with a difference value of 0 in the second application condition.

The horizontal axis of FIG. 16 illustrates the energy value (key), and the vertical axis of FIG. 16 illustrates the peak value. In the example illustrated in FIG. 16, the first feature point of the detection element A in the first application condition is set as the peak value A1, and the second feature point of the detection element A in the second application condition is set as the peak value B1. Also in the example illustrated in FIG. 16, the first feature point of the detection element B in the first application condition is set as the peak value A2, and the second feature point of the detection element B in the second application condition is set as the peak value B2. Also in the example illustrated in FIG. 16, the first feature point the detection element C in the first application condition is set as the peak value A3, and the second feature point of the detection element C in the second application condition is set as the peak value B3.

The energy and the peak value have linear relation, as illustrated with reference to FIG. 9. For example, suppose that the peak value is An, the energy is En, the gain is $\alpha$, and the offset is $\beta$, then the relation "$An=\alpha En+\beta$" is satisfied. For this reason, the calculating function 33a calculates the gain ($\alpha$) and the offset ($\beta$) of each of the detection elements, by plotting the peak value and the energy as illustrated in FIG. 16. In such a case, the energy value E1 with the difference value of 0 in the first application condition and the energy value E2 with the difference value of 0 in the second application condition are set in advance. For example, the energy value E1 and the energy value E2 are measured in advance using a detector (also referred to as "reference detector") having high energy resolution, such as a GE detector.

More specifically, the reference detector has high energy resolution, and is capable of detecting characteristic X rays. In addition, the energy value of the characteristic X rays is known. Specifically, the energy value of the characteristic X-rays detected with the reference detector is a value that can be specified. In the example illustrated in FIG. 16, E3 is the energy value of characteristic X-rays detected with the reference detector, and C3 is the peak value of the characteristic X-rays detected with the reference detector.

In addition, the reference detector calculates the peak value C1 with the difference value of 0 in the first application condition and the peak value C2 with the difference value of 0 in the second application condition. The peak values C1 and C3 and the energy values E1 and E3 have the relation "C3:E3=C1:E1". Because the values other than E1 are known, the energy value E1 with the difference value of 0 in the first application condition is calculated using "E1=C1*E3/C3". In the same manner, the peak values C2 and C3 and the energy values E2 and E3 have the relation "C3:E3=C2:E2". Because the values other than E2 are known, the energy value E2 with the difference value of 0 in the second application condition is calculated using "E2=C2*E3/C3".

The calculating function 33a calculates the correction value by linear regression using the first feature point and the second feature point. The calculating function 33a calculates the gain ($\alpha$) and the offset ($\beta$) of each of the detection elements from the relation "$An=\alpha En+\beta$"" described above, using the energy values calculated using the reference detector. In other words, the calculating function 33a determines the energy value of the first feature point and the energy value of the second feature point from a plurality of signals detected using reference detection elements having energy resolution higher than that of the detection elements included in the photon counting detector to calculate the correction value. Thereafter, the calculating function 33a stores the gain ($\alpha$) and the offset ($\beta$) calculated for each of the detection elements, as the correction value, in the correction value storage circuitry 142.

Thereafter, the waveform shaping circuitry 143 calibrates the detection signal of each of the detection elements using the correction value based on a result of arithmetic processing using a plurality of signals output from the detection element under a plurality of X-ray application conditions.

Second Embodiment

The first embodiment and the modification of the first embodiment illustrate the structure in which the energy value in the feature point is measured in advance. Instead of using the energy value measured in advance, the energy value in the feature point may be measured in real time using reference detection elements having energy resolution higher than that of the X-ray detection elements included in the detector 13 to calibrate each of the X-ray detection element. For this reason, the second embodiment illustrates the case of using reference detection elements having high energy resolution in combination in the detector 13. Specifically, the photon counting detector 13 according to the second embodiment includes reference detection elements in at least part of the detection elements.

The configuration of the X-ray CT apparatus according to the second embodiment is similar to the configuration of the X-ray apparatus illustrated in FIG. 1, except that the structure of the X-ray detection elements included in the detector 13 and the structure of the data collection circuitry 14 are different from the first embodiment, and the structure of the scan control circuitry 33 is different from the first embodiment. For this reason, the following explanation illustrates only the structure of the detector 13 according to the second embodiment, the structure of the data collection circuitry 14 according to the second embodiment, and the structure of the scan control circuitry 33 according to the second embodiment. The X-ray CT apparatus according to the second embodiment has a structure in which only the detector 13 is movable on the rotary frame 15.

Figure 17:
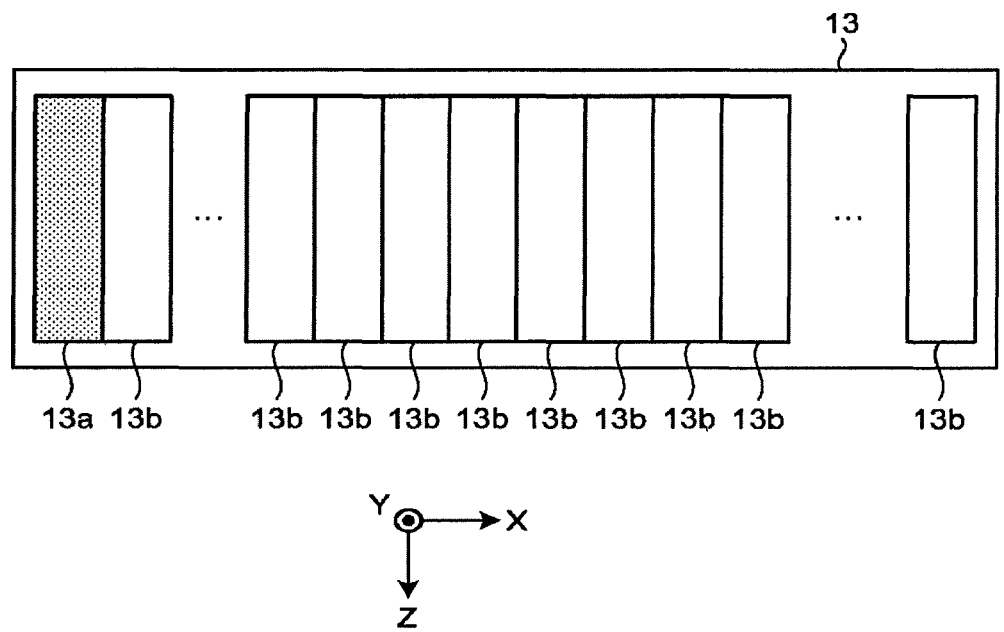
FIG. 17 is a diagram for explaining an example of the detector according to a second embodiment.

FIG. 17 is a diagram for explaining an example of the detector 13 according to the second embodiment. FIG. 17 illustrates the detector 13 as viewed from the Y-axis side. In the detector 13, X-ray detection elements are arranged on a surface in a two-dimensional manner. For example, a plurality of lines of X-ray detection elements arranged in the channel direction (X-axis direction in FIG. 17) are arranged along the body axis direction (Z-axis direction illustrated in FIG. 17) of the subject P. The example of FIG. 17 illustrates the X-ray detection elements arranged along the body axis direction as one X-ray detection element group.

As illustrated in FIG. 17, the detector 13 according to the second embodiment includes one X-ray detection element group 13a, and a plurality of X-ray detection element groups 13b. In the example illustrated in FIG. 17, the X-ray detection element group 13a is disposed in one end portion in the channel direction in the detector 13. Each of X-ray detection elements of the X-ray detection element groups 13b is an indirect conversion detector formed of a scintillator and an optical sensor. The optical sensor is, for example, a SiPM. Each of the X-ray detection elements of the X-ray detection element group 13a is a reference detection element having energy resolution higher than that of each X-ray detection element of the X-ray detection element groups 13b. Each of X-ray detection elements of the X-ray detection element group 13a is, for example, a direct conversion detector that can be formed of cadmium telluride (CdTe) or cadmium zinc telluride (CdZnTe).

Figure 18:
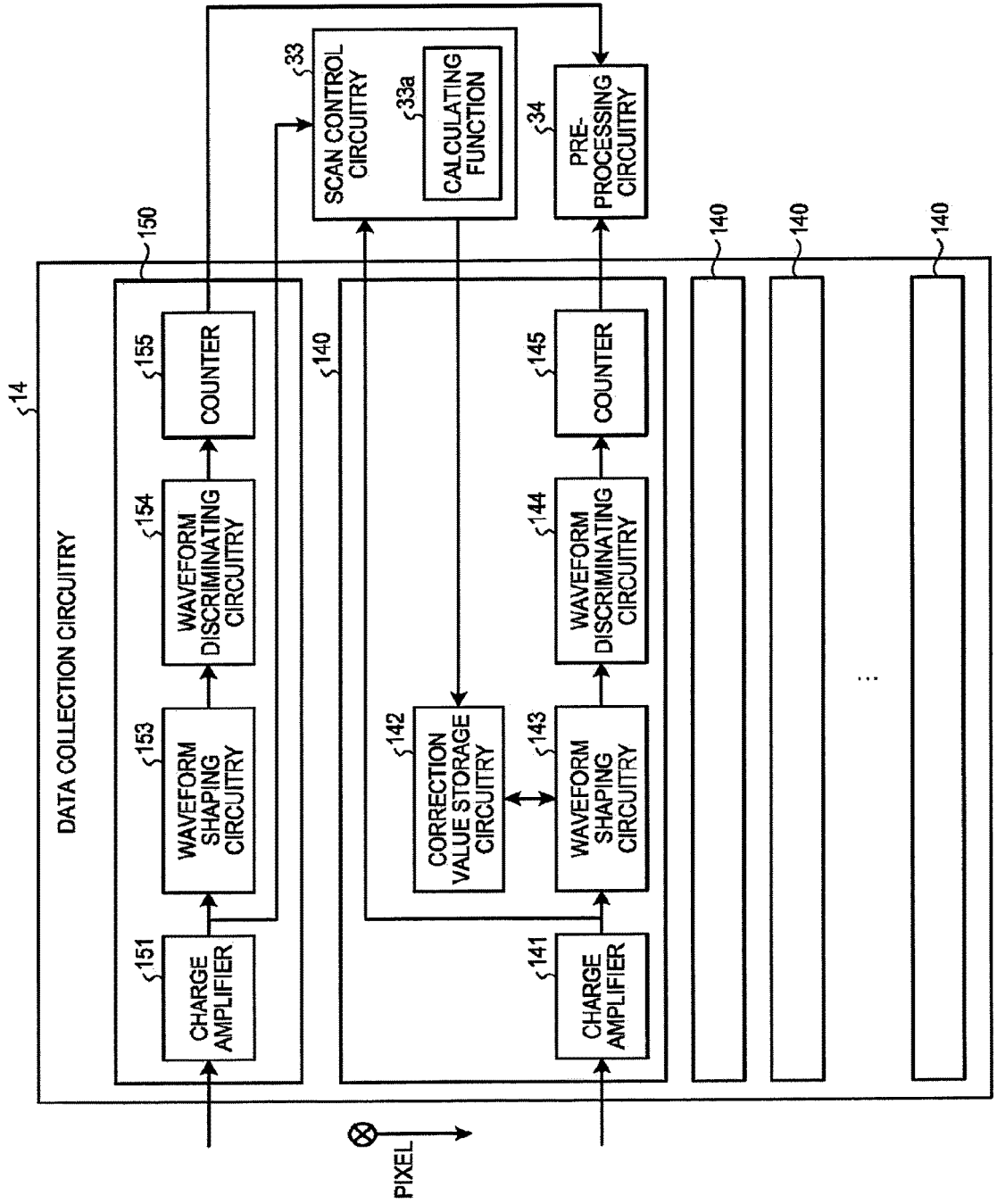
FIG. 18 is a diagram illustrating a configuration example of the data collection circuitry according to the second embodiment.

FIG. 18 is a diagram illustrating a configuration example data collection circuitry 14 according to the second embodiment. As illustrated in FIG. 18, the data collection circuitry 14 includes the collection units 140 and a collection unit 150.

The collection units 140 correspond to the respective X-ray detection elements of the X-ray detection element groups 13b. Accordingly, the number of collection units 140 provided is equal to the number of X-ray detection elements of the X-ray detection element groups 13b. Each of the collection units 140 includes a charge amplifier 141, correction value storage circuitry 142, waveform shaping circuitry 143, waveform discriminating circuitry 144, and a counter 145. The functions of the elements included in the collection units 140 according to the second embodiment are the same as the functions of the elements included in the collection units 140 according to the second embodiment.

The collection unit 150 corresponds to the respective X-ray detection elements of the X-ray detection element group 13a. Accordingly, the number of collection units 150 provided is equal to the number of X-ray detection elements of the X-ray detection element group 13a. Each of the collection units 150 includes a charge amplifier 151, waveform shaping circuitry 153, waveform discriminating circuitry 154, and a counter 155.

The charge amplifier 151 integrates and amplifies a charge collected in response to the photon made incident on each of the X-ray detection elements of the X-ray detection element group 13a, and outputs the charge as a pulse signal of the electric quantity. The output side of the charge amplifier 151 is connected with the waveform shaping circuitry 153 and the scan control circuitry 33. The charge amplifier 151 outputs the pulse signal to the calculating function 33a of the scan control circuitry 33, in the case of performing processing of calculating a correction value. In this manner, the calculating function 33a calculates a correction value. By contrast, when the pixel corresponding to the reference detection element disposed in one end portion in the channel direction is used for reconstruction of an X-ray CT image, the charge amplifier 151 outputs the pulse signal to the waveform shaping circuitry 153.

The waveform shaping circuitry 153 adjusts the frequency characteristic of the pulse signal output from the charge amplifier 151, and supplies the gain and the offset to shape the waveform of the pulse signal.

The waveform discriminating circuitry 154 is circuitry comparing the wave height or the area of the response pulse signal for the incident photon with preset thresholds corresponding to a plurality of energy bands to be discriminated, and outputting a result of comparison with the thresholds to the following counter 155.

The counter 155 counts a discrimination result of the waveform of the response pulse signals for each of the corresponding energy bands, and outputs a photon counting result as digital data to the preprocessing circuitry 34 of the console 30.

Figure 19:
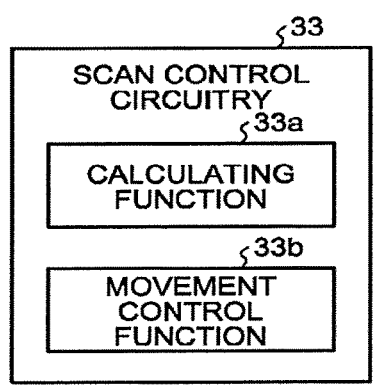
FIG. 19 is a diagram illustrating a configuration example of scan control circuitry according to the second embodiment.

FIG. 19 is a diagram illustrating a configuration example of the scan control circuitry 33 according to the second embodiment. As illustrated in FIG. 19, the scan control circuitry 33 according to the second embodiment performs the calculating function 33a and a movement control function 33b. For example, each of processing functions executed with the calculating function 33a and the movement control function 33b serving as constituent elements of the scan control circuitry 33 illustrated in FIG. 19 are recorded in the scan control circuitry 33, in the form of programs executable by a computer. The scan control circuitry 33 is a processor reading and executing each of the programs, to achieve the function corresponding to the read program. In other words, the scan control circuitry 33 in the state of reading the programs has the functions illustrated in the scan control circuitry 33 of FIG. 19.

Figure 20:
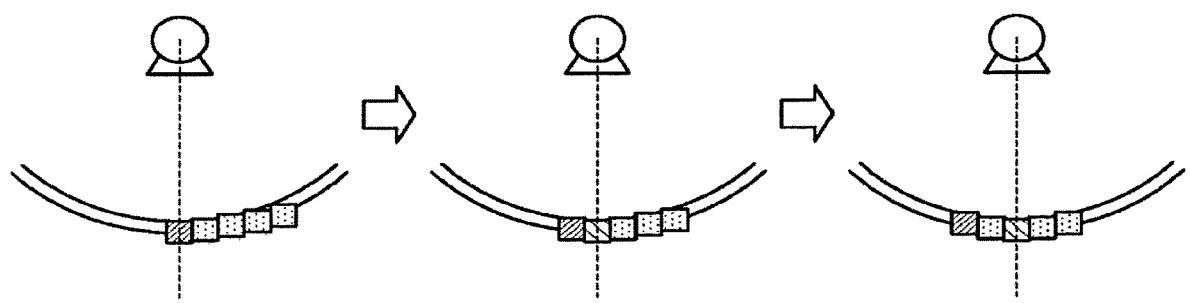
FIG. 20 is a diagram for explaining a processing operation of a movement control function according to the second embodiment.

The movement control function 33b controls movement of the detector 13 in the channel direction, independently of the X-ray tube 12. In other words, the movement control function 33b moves the detector 13 alone in the channel direction on the rotary frame 15. FIG. 20 is a diagram for explaining a processing operation of the movement control function 33b according to the second embodiment. The left drawing in FIG. 20 illustrates the case where the reference detection element is disposed in a position opposed to the X-ray tube 12. In this state, X-rays are applied from the X-ray tube 12 under a plurality of X-ray application conditions, and the reference detection element detects X-ray spectrum under each of the X-ray application conditions. Specifically, the movement control function 33b positions the reference detection element in a position opposed to the X-ray tube 12 when the energy value in the feat re point is calculated using the count value of the first signal and the count value of the second signal detected with the reference detection element.

Thereafter, the movement control function 33b moves the detector 13 in the channel direction. In this manner, the X-ray detection element of the X-ray detection element group 13b disposed adjacent to the reference detection element is positioned in a position opposed to the X-ray tube 12, as illustrated in the middle drawing of FIG. 20. In this state, X-rays are applied from the X-ray tube 12 under a plurality of X-ray application conditions, and the X-ray detection element of the X-ray detection element group 13b detects X-ray spectrum under each of the X-ray application conditions. Specifically, the movement control function 33b positions the X-ray detection element to be calibrated in a position opposed to the X-ray tube 12, when the feature point is specified using the count value of the first signal and the count value of the second signal detected with the X-ray detection element to be calibrated.

In the same manner, the movement control function 33b moves the detector 13 in the channel direction. In this manner, the X-ray detection element of the second X-ray detection element group 13b from the reference detection element is positioned in a position opposed to the X-ray tube 12, as illustrated in the right drawing of FIG. 20. In this Late, X-rays are applied from the X-ray tube 12 under a plurality of X-ray application conditions, and the X-ray detection element of the X-ray detection element group 13b detects X-ray spectrum under each of the X-ray application conditions. Specifically, the movement control function 33b positions the X-ray detection element to be calibrated in a position opposed to the X-rap tube 12, when the feature point is specified using the count value of the first signal and the count value of the second signal detected with the X-ray detection element to be calibrated, in the same manner as the case illustrated in the middle drawing of FIG. 20. As described above, the movement control function 33b moves position of the detector 13 in the channel direction, without moving the position of the X-ray tube 12. The movement control function 33b performs control such that the position of the reference detection element in the channel direction at the time when the feature point is specified agrees with the position of the X-ray detection element in the channel direction at the time when the feature point is specified from the detection signal detected with the X-ray detection element to be calibrated.

As described above, the movement control function 33b controls movement of the photon counting X-ray detector in the channel direction independently of the X-ray tube 12. In addition, the movement control function 33b performs control such that the position of the reference detection element in the channel direction at the time when the energy value of the first feature point and the energy value of the second feature point are determined agrees with the position of the X-ray detection element in the channel direction at the time when the first feature point and the second feature point are specified from a plurality of signals detected with the X-ray detection element to be calibrated. For example, when the energy value of the first feature point and the energy value of the second feature point are determined, the movement control function 33b positions the reference detection element in a position opposed to the X-ray tube 12. In addition, when the first feature point and the second feature point are specified from a plurality of signals detected with the X-ray detection element to be calibrated, the movement control function 33b positions the detection element to be calibrated in a position opposed to the X-ray tube 12.

The calculating function 33a according to the second embodiment is capable of performing a function similar to that of the calculating function 33a explained in the first embodiment, and the calculating function 33a according to the modification of the first embodiment. For example, the calculating function 33a according to the second embodiment may specify the peak value at which the ratio of the count value of the first signal and the count value of the second signal has a predetermined value, as the feature point. As another example, the calculating function 33a according to the second embodiment may specify the peak value among a plurality of signals at which the count value of the first signal collected under existence of the filter removing X-rays of a predetermined band is equal to the count value of the second signal collected under absence of the filter.

In addition, the calculating function 33a according to the second embodiment specifies the peak value of the feature point from the detection signal detected with the X-ray detection element to be calibrated. For example, the calculating function 33a according to the second embodiment specifies the peak value in the first feature point and the peak value in the second feature point, for each of the detection elements.

In addition, the calculating function 33a according to the second embodiment specifies the feature point and the characteristic X-rays from the detection signal detected using the reference detection element, and calculates the energy value in the feature point from the peak value in the feature point, the peak value of the characteristic X-rays, and the energy value of the characteristic X-rays. For example, the calculating function 33a according to the second embodiment calculates the energy value in the first feature point and the energy value in the second feature point, from the peak value in the first feature point, the peak value in the second feature point, the peak value of the characteristic X-rays, and the energy value of the characteristic X-rays. In addition, the calculating function 33a according to the second embodiment calculates the correction value for each of the detection elements by linear regression using the first feature point and the second feature point.

Thereafter, the waveform shaping circuitry 143 of the data collection circuitry 14 calibrates the detection signal detected with the photon counting detector 13 for each of the X-ray detection element on the basis of the correction value. The image reconstruction circuitry 36 reconstructs X-ray image data on the basis of the calibrated detection signal. Specifically, the image reconstruction circuitry 36 generates an image using the calibrated detection signals of the detection elements. The system control circuitry 38 displays the reconstructed X-ray CT image on the display 32. The process of processing of reconstructing an X-ray CT image with the X-ray CT apparatus according to the second embodiment is similar to the process illustrated in FIG. 12, and the detailed explanation thereof is omitted.

Figure 21:
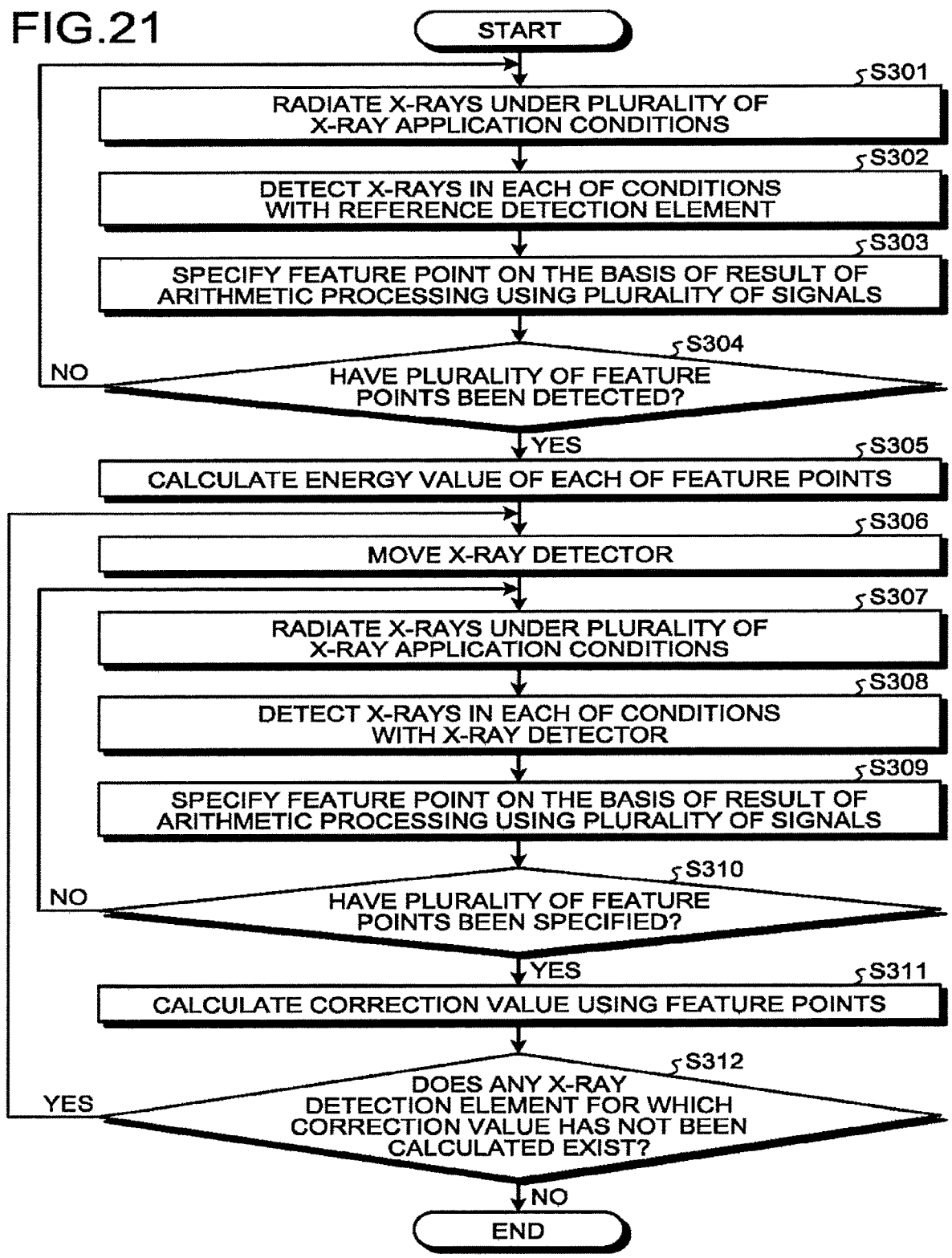
FIG. 21 is a flowchart illustrating a process of processing of calculating a correction value performed by the X-ray CT apparatus according to the second embodiment.

FIG. 21 is a flowchart illustrating processing of calculating the correction value with the X-ray CT apparatus according to the second embodiment. The example of FIG. 21 illustrates the case in which the reference detection element having high energy resolution is positioned in a position opposed to the X-ray tube 12 at the point in time of starting the processing of calculating the correction value.

Step S301 is a step achieved with the scan control circuitry 33. At Step S301, the scan control circuitry 33 controls the X-ray tube 12 to cause the X-ray tube 12 to radiate X-rays under a plurality of X-ray application conditions. For example, the scan control circuitry 33 applies X-rays under two X-ray application conditions with different tube voltages of 80 KV and 140 KV, as the first application condition. The scan control circuitry 33 may apply X-rays with the tube voltage of 140 KV under presence of the filter removing X-rays of a predetermined band, and apply X-rays with the tube voltage of 80 KV under absence of the filter.

Step S302 is a step achieved with the detector 13. At Step S302, the reference detection element of the detector 13 detects X-rays in each of the conditions. For example, the reference detection element of the detector 13 detects X-rays radiated with the X-ray application condition with the tube voltage of 140 KV as the first signal, and detects X-rays radiated with the X-ray application condition with the tube voltage of 80 KV as the second signal. The reference detection element of the detector 13 may detect X-rays as the first signal under presence of the filter, and detect X-rays as the second signal under absence of the filter.

Step S303 to Step S305 are steps corresponding to the calculating function 33a. The calculating function 33a is achieved by the scan control circuitry 33 calling and executing a predetermined program stored in the scan control circuitry 33. At step S303, the calculating function 33a specifies the feature point on the basis of a result of arithmetic processing using a plurality of signals. For example, the calculating function 33a calculates the ratio of the count value of the first signal to the count value of the second signal among a plurality of signals, and specifies the peak value at which the calculated ratio has a predetermined value, as the feature point. The calculating function 33a may specify the peak value at which the count value of the first signal collected under presence of the filter is equal to the count value of the second signal collected under absence of the filter, as the feature point.

At Step S304, the calculating function 33a determines whether a plurality of feature points have been specified. When it is determined that a plurality of feature points have been specified for the reference detection element (Yes at Step S304), the calculating function 33a proceeds to Step S305. By contrast, when it is determined that a plurality of feature points have not been specified for the reference detection element (No at Step S304), the calculating function 33a proceeds to Step S301. In such a case, for example, the scan control circuitry 33 causes radiation of X-rays under the second application condition different from the first application condition.

At Step S305, the calculating function 33a calculates the energy value of each of the feature points. For example, the calculating function 33a specifies the feature point and the characteristic X-rays from the detection signal detected using the reference detection element, and calculates the energy value in the feature point from the peak value in the feature point, the peak value of the characteristic X-rays, and the energy value of the characteristic X-rays.

Step S306 is a step corresponding to the movement control function 33b. The movement control function 33b is achieved by the scan control circuitry 33 calling and executing the predetermined program stored in the scan control circuitry 33. At Step S306, the movement control function 33b moves the detector 13. For example, the movement control function 33b moves the detector 13 by one detection element group. In this manner, the detection element to be calibrated and disposed next to the reference detection element is positioned in a position opposed to the X-ray tube 12.

Step S307 is a step achieved with the scan control circuitry 33. At Step S307, the scan control circuitry 33 controls the X-ray tube 12 to cause the X-ray tube 12 to radiate X-rays under a plurality of X-ray application conditions. For example, the scan control circuitry 33 causes radiation of X-rays under the same X-ray application conditions as those of Step S301. Step S308 is a step achieved with the detector 13. At Step S308, the detection element to be calibrated in the detector 13 detects X-rays in each of the conditions.

Step S309 to Step S311 are steps corresponding to the calculating function 33a. The calculating function 33a is achieved by the scan control circuitry 33 calling and executing a predetermined program stored in the scan control circuitry 33. At step S309, the calculating function 33a specifies the feature point on the basis of a result of arithmetic processing using a plurality of signals. For example, the calculating function 33a specifies a feature point on the basis of a result of arithmetic processing using a plurality of signals. For example, the calculating function 33a specifies the feature point in the same manner as in Step S303.

At Step S310, the calculating function 33a determines whether a plurality of feature points have been specified. When it is determined that a plurality of feature points have been specified for the detection element to be calibrated (Yes at Step S310), the calculating function 33a proceeds to Step S311. By contrast, when it is determined that a plurality of feature points have not been specified for the detection element to be calibrated (No at Step S310), the calculating function 33a proceeds to Step S307. In such a case, for example, the scan control circuitry 33 causes radiation of X-rays under the second application condition different from the first application condition.

At Step S311, the calculating function 33a calculates the correction value using the feature points. For example, the calculating function 33a calculates the correction value by linear regression using the first feature point and the second feature point.

Step S312 is a step achieved with the scan control circuitry 33. At Step S312, the scan control circuitry 33 determines whether any X-ray detection element for which the correction value has not been calculated exists (Step S312). When it is determined that any X-ray detection element for which the correction value has not been calculated exists (Yes at Step S312), the scan control circuitry 33 proceeds to Step S306, In this manner, the movement control function 33b moves the detector 13 by one detection element group, and calculates the correction value of the X-ray detection element positioned in the application position. By contrast, when it is determined that no X-ray detection element for which the correction value has not been calculated exists (No at Step S312), the scan control circuitry 33 ends the processing of calculating the correction value.

As described above, in the second embodiment, the X-ray CT apparatus calculates the energy value of the feature point using the detection signal detected with the reference detection element, and specifies the peak value of the feature point from the signal detected using the X-ray detection element to be calibrated. In addition, in the second embodiment, the X-ray CT apparatus calibrates the detection signal of each of the detection elements using the correction value based on a result of arithmetic processing using a plurality of signals output front the X-ray detection elements under a plurality of X-ray application conditions. As described above, the second embodiment enables simple and more accurate calibration by measuring the energy value in the feature point in real time using the reference detection element included in the detector 13, and calculating the correction value of each of the X-ray detection elements.

X-ray detection elements having high energy resolution such as CdTe are expensive and difficult to mass-produce. For this reason, the use of CdTe has not spread enough to be used for a large-scale area detector. By contrast, there are cases where actual reconstruction of an X-ray CT image does not require energy resolution as high as that of CdTe. However, even X-ray detection elements having energy resolution lower than that of CdTe also require proper calibration. In the second embodiment, reference detection elements having high energy resolution is integrated in the detector 13, and a correction value is calculated for each of the detection elements on the basis of the energy value of the feature point measured with the reference detection element having high energy resolution to calibrate the detection signal detected with each of the detection elements. Specifically, in the second embodiment, a detection signal detected with an inexpensive X-ray detection element formed of a SiPM and a scintillator is corrected for each of the X-ray detection elements to reconstruct the X-ray CT image. In this manner, the second embodiment enables both reduction in cost and collection of image data with accuracy.

The second embodiment illustrates the case of including the reference detection elements in the detector 13, but the embodiment is not limited thereto. For example, the reference detection elements may be disposed in a place other than the detector 13, as long as the reference detection elements are disposed in a position in which they can measure X-ray spectrum applied from the X-ray tube 12. In such a case, the calculating function 33a performs calibration on the detection signal of the reference detection element to a detection signal in the case where the reference detection element is positioned in a position opposed to the X-ray tube 12, to calculate the energy value of the feature point.

In addition, the second embodiment illustrates the structure in which the reference detection elements are disposed in one end portion in the channel direction in the detector 13, but the embodiment is not limited thereto. For example, the reference detection elements may be disposed in a desired position, such as the center position in the channel direction in the detector 13. When the reference detection elements are disposed in one end portion in the channel direction in the detector 13, the detection signal from the reference detection signal may not be used for reconstruction of an X-ray CT image.

Figure 22:
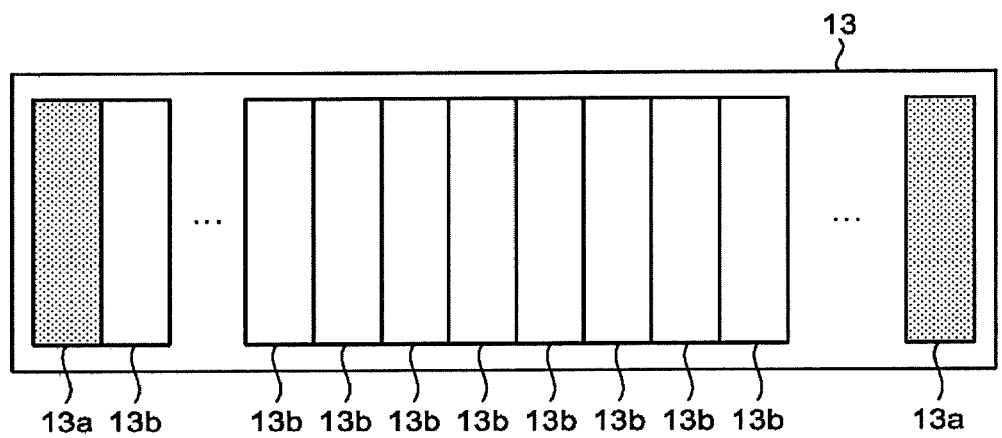
FIG. 22 is a diagram for explaining another example of the detector according to the second embodiment.
Figure 23:
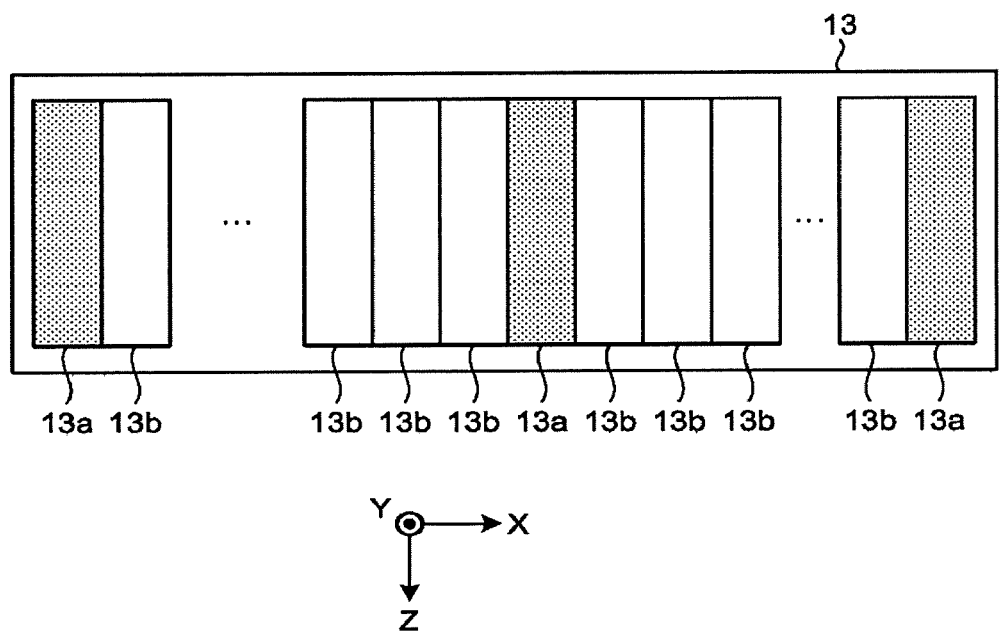
FIG. 23 is a diagram for explaining another example of the detector according to the second embodiment.

FIG. 22 and FIG. 23 are diagrams for explaining another example of the detector according to the second embodiment. In the example illustrated in FIG. 22, the X-ray detection element group 13a is disposed in each of end portions in the channel direction in the detector 13. In the example illustrated in FIG. 23, the X-ray detection element group 13a is disposed in each of end portions in the channel direction in the detector 13, and in the center portion in the channel direction in the detector 13.

Modification of Second Embodiment

The second embodiment described above illustrates the case of positioning the reference detection element in a position opposed to the X-ray tube 12 to perform calibration, but the embodiment is not limited thereto. For example, when the position opposed to the X-ray tube 12 in the detector 13 is defined as center portion, and a position around the center portion is defined as peripheral portion, the radiation quality of X-rays detected in the center portion is different from the radiation quality of X-rays detected in the peripheral portion. In addition, the radiation quality of detected X-rays is different in each of positions in the peripheral portion. In other words, the radiation quality of detected X-rays differs according to the relative positional relation between the X-ray tube 12 and each X-ray detection element.

Figure 24:
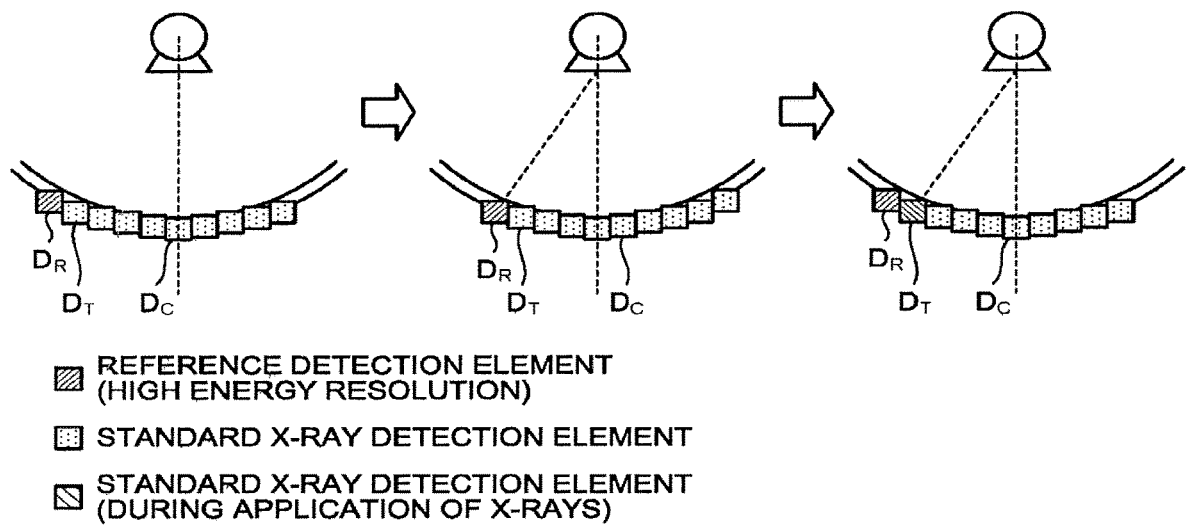
FIG. 24 is a diagram for explaining a processing operation of the movement control function according to a modification of the second embodiment.

For this reason, calibration is desirably performed while maintaining the relative position between each of X-ray detection elements of the X-ray detection element group 13b and the X-ray tube 12. For this reason, the following is an explanation of performing calibration while maintaining the relative position between each of X-ray detection elements and the X-ray tube 12, as a modification of the second embodiment. The structure of the X-ray CT apparatus according to the modification of the second embodiment is similar to the structure of the X-ray CT apparatus according to the second embodiment, except that part of function of the movement control function 33b is different from that of the second embodiment. FIG. 24 is a diagram for explaining a processing operation of the movement control function 33b according to the modification of the second embodiment.

FIG. 24 illustrates the case where reference detection elements are arranged at left end as one end portion in the channel direction, in the same manner as the detector 13 illustrated in FIG. 17. In addition, FIG. 24 illustrates the case of performing calibration on X-ray detection element $D_T$ disposed on the right side of the reference detection element $D_R$ in the channel direction. In the left drawing in FIG. 24, the X-ray detection element $D_C$ disposed in the center of the detector 23 is positioned in a position opposed to the X-ray tube 12. The state of the left drawing in FIG. 24 serves as initial state.

The movement control function 33b controls movement of the detector 13 in the channel direction, independently of the X-ray tube 12. In addition, the movement control function 33b performs control such that the position of the reference detection element in the channel direction at the time when the energy value is calculated in the feature point using the count value of the first signal and the count value of the second signal detected with the reference detection element agrees with the position of the X-ray detection element to be calibrated in the channel direction at the time when the feature point is specified using the count value of the first signal and the count value of the second signal detected with the X-ray detection element to be calibrated.

For example, the movement control function 33b moves the detector 13 to the right in the channel direction, by a distance corresponding to one X-ray detection element. The movement control function 33b moves the position of the detector 13 in the channel direction, without moving the position of the X-ray tube 12, in the same manner as the second embodiment. In this manner, the reference detection element $D_R$ is moved to the position in which the X-ray detection element $D_T$ was positioned before the movement. In this state, the X-ray tube 12 applies X-rays under a plurality of X-ray application conditions, and the reference detection element $D_R$ detects X-ray spectrum in each of the X-ray application conditions. Specifically, when the energy value in the feature point is calculated, the movement control function 33b positions the reference detection element $D_R$ in a position agreeing with the relative position between the X-ray detection element $D_T$ to be calibrated and the X-ray tube 12 in the state in which the center of the photon counting detector 13 is opposed to the X-ray tube 12.

Thereafter, the movement control function 33b moves the detector 13 to the left in the channel direction, by a distance corresponding to one X-ray detection element. Also in such a case, the movement control function 33b moves the position of the detector 13 in the channel direction, without moving the position of the X-ray tube 12, in the same manner as the second embodiment. In this manner, the X-ray detection element $D_T$ is positioned in the same position as that of the initial state. In this state, the X-ray tube 12 applies X-rays under a plurality of X-ray application conditions, and the X-ray detection element $D_T$ detects X-ray spectrum in each of the X-ray application conditions. Specifically, when the feature point is specified from the detection signal detected with the X-ray detection element $D_T$ to be calibrated, the movement control function 33b positions the center of the photon counting detector 13 in a position opposed to the X-ray tube 12.

As described above, when the energy value of the first feature point and the energy value of the second feature point are determined, the movement control function 33b according to the modification of the second embodiment positions the reference detection element in a position agreeing with the relative position between the detection element to be calibrated and the X-ray tube 12, in the state in which the center of the photon counting detector 13 is opposed to the X-ray tube 12. In addition, the movement control function 33b according to the modification of the second embodiment positions the center of the photon counting detector 13 in a position opposed to the X-ray tube 12 when the first feature point and the second feature point are specified from a plurality of signals detected with the detection element to be calibrated.

Thereafter, the calculating function 33a according to the modification of the second embodiment calculates the energy value in the feature point from the detection signal detected using the reference detection element $D_R$, and specifies the peak value of the feature point from the signal detected using the X-ray detection element $D_T$ to be calibrated. Thereafter, the calculating function 33a according to the modification of the second embodiment calculates the correction value for each of the detection elements by linear regression using the first feature point and the second feature point.

Thereafter, the waveform shaping circuitry 143 of the data collection circuitry 14 calibrates the detection signal detected with the photon counting detector 13 for each of the X-ray detection elements on the basis of the correction value. In this manner, the modification of the second embodiment enables calibration while maintaining the relative position between each of the X-ray detection elements of the X-ray detection element group 13b and the X-ray tube 12.

In the modification of the second embodiment described above, the reference detection element $D_R$ is moved to a position in which the X-ray detection element $D_T$ to be calibrated is disposed in the initial state to apply X-rays, and thereafter the state is returned to the initial state to apply X-rays to the X-ray detection element $D_T$ to be calibrated, but the embodiment is not limited thereto. Specifically, the detector 13 may be moved in a desired order, as long as the reference detection element $D_R$ is moved while the relative position between the X-ray detection element to be calibrated and the X-ray tube 12 is maintained. For example, in the initial state, the X-ray tube 12 applies X-rays, and each of the X-ray detection element to be calibrated detects X-ray spectrum. Thereafter, after the reference detection element $D_R$ is moved to the position the X-ray detection element to be calibrated was disposed in the initial state, the X-ray tube 12 applies X-rays, and the reference detection element $D_R$ detects X-ray spectrum. The movement control function 33b repeats the processing in the predetermined order, until the reference detection element $D_R$ detects X-ray spectrum in all the positions in which the X-ray detection elements to be calibrated are disposed in the initial state.

The modification of the second embodiment illustrates the case of using the detector 13 similar to that of FIG. 17, but the embodiment is not limited thereto. For example, the detector 13 as illustrated in FIG. 22 or FIG. 23 may be used. In such a case, because calibration is possible using a plurality of reference detection elements, this structure reduces the number of movements of the detector 13 and the number of applications of X-rays.

Third Embodiment

Figure 25:
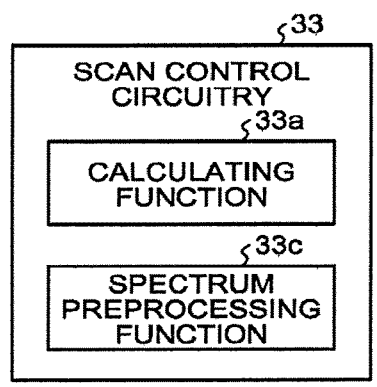
FIG. 25 is a diagram illustrating a configuration example of the scan control circuitry according to a third embodiment.

The embodiments described above illustrate the structure in which the calculating function 33a specifies the feature point on the basis of a result of arithmetic processing using the X-ray spectrum detected with the detection element or the reference detection element, and calculates the correction value using the feature point. But the embodiments are not limited thereto. For example, the calculating function 33a may specify the feature point on the basis of a result of arithmetic processing using X-ray spectrum after being subjected to preprocessing such as noise reduction, and calculate the correction value using the feature point. FIG. 25 is a diagram illustrating a configuration example of the scan control circuitry 33 according to a third embodiment.

As illustrated in FIG. 25, the scan control circuitry 33 according to the third embodiment executes the calculating function 33a and a spectrum preprocessing function 33c. For example, the processing functions executed with the calculating function 33a and the spectrum preprocessing function 33c serving as the constituent elements of the scan control circuitry 33 illustrated in FIG. 25 are recorded in the scan control circuitry 33, in the form of programs executable with a computer. The scan control circuitry 33 is a processor that reads and executes each of the programs to achieve the function corresponding to the read program. In other words, the scan control circuitry 33 in the state of reading the programs has the functions illustrated in the scan control circuitry 33 of FIG. 25.

Figure 26:
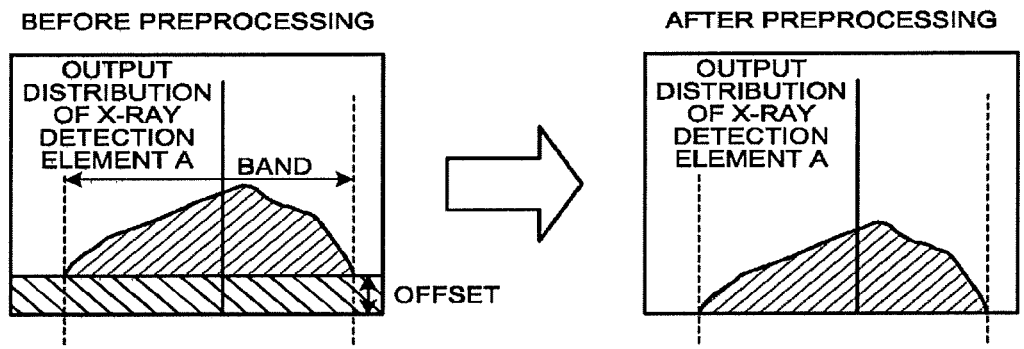
FIG. 26 is a diagram for explaining a processing operation of a spectrum processing function according to the third embodiment.
Figure 27:
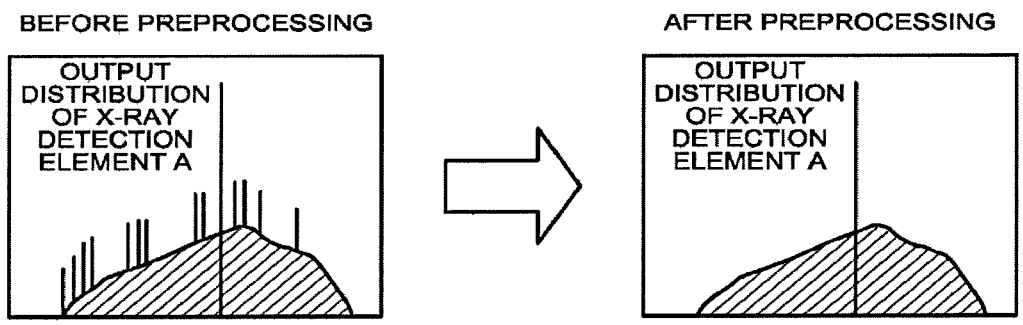
FIG. 27 is a diagram for explaining a processing operation of the spectrum processing function according to the third embodiment.

The spectrum preprocessing function 33c preprocesses a plurality of signals. FIG. 26 and FIG. 27 are diagrams for explaining the processing operation of the spectrum preprocessing function 33c according to the third embodiment. FIG. 26 and FIG. 27 illustrate the case of preprocessing the X-ray spectrum detected with the reference detection element.

FIG. 26 illustrates the processing of removing offset The left drawing in FIG. 26 illustrates the X-ray spectrum detected with the X-ray detection element A serving as the reference detection element, and serving as a standard before preprocessing. The spectrum preprocessing function 33c removes the offset, to generate the X-ray spectrum illustrated in the right drawing in FIG. 26. The spectrum preprocessing function 33c determines the upper limit value of the band of the X-ray spectrum as follows. For example, the spectrum preprocessing function 33c estimates the upper limit of the energy value on the basis of the tube voltage of the X-ray tube 12, and removes X-ray spectrum having an energy value equal to or higher than the estimated upper limit value. In addition, the spectrum preprocessing function 33c determines the lower limit value of the band of the X-ray spectrum as follows. For example, the spectrum preprocessing function 33c removes X-ray spectrum having energy value equal to or lower than the energy value removed with a bowtie filter that is not illustrated.

FIG. 27 illustrates smoothing processing. The left drawing in FIG. 27 illustrates X-ray spectrum detected with the X-ray detection element A serving as the reference detection element, and serving as a standard before preprocessing. The spectrum preprocessing function 33c removes noise of the X-ray spectrum illustrated in the left drawing of FIG. 27, to generate X-ray spectrum with a stable mean value as illustrated in the right drawing of FIG. 27.

The calculating function 33a according to the third embodiment calculates a correction value based on a result of arithmetic processing using a plurality of signals after preprocessing, for each of the K-ray detection elements As described above, performing preprocessing on the X-ray spectrum enables calculation of more accurate correction value. Thereafter, the waveform shaping circuitry 143 of the data collection circuitry 14 calibrates the detection signal detected with the photon counting detector 13, for each of the X-ray detection elements. In other words, the waveform shaping circuitry 143 calibrates the detection signal of each of the detection elements using the correction value calculated from a plurality of signals after preprocessing.

The third embodiment illustrates the case of preprocessing the X-ray spectrum detected with the reference detection element, but the embodiment is not limited thereto. For example, the spectrum preprocessing function 33 according to the third embodiment may preprocess the X-ray spectrum detected with the reference detection element, and the X-ray spectrum detected with each of the X-ray detection elements to be calibrated. In such a case, the calculating function 33a according to the third embodiment calculates the energy value in the feature point from the X-ray spectrum detected with the reference detection element and subjected to preprocessing, and specifies the peak value of the feature point from the X-ray spectrum detected with the X-ray detection element to be calibrated and subjected to preprocessing. The calculating function 33a according to the third embodiment calculates the correction value for each of the detection elements by linear regression using the first feature point and the second feature point. The spectrum preprocessing function 33c according to the third embodiment may preprocess only the X-ray spectrum detected with the photon counting detector 13, without preprocessing the X-ray spectrum detected with the reference detection element.

Other Embodiment

The embodiments are not limited to the embodiments described above.

The first to the third embodiments described above illustrate the structure in which the charge amplifier 141 outputs the pulse signal to the calculating function 33a of the scan control circuitry 33 in the case of performing processing of calculating a correction value, but the embodiments are not limited thereto. For example, the waveform shaping circuitry 143 may output the pulse signal to the calculating function 33a of the scan control circuitry 33. In such a case, the waveform shaping circuitry 143 switches the output of the pulse signal to one of the scan control circuitry 33 and the waveform discriminating circuitry 144 in accordance with an instruction of the scan control circuitry 33.

In addition, the first to the third embodiments described above illustrate the structure in which the X-ray CT apparatus calculates a correction value, but the embodiments are not limited thereto. For example, in the image processing methods explained in the first embodiment to the third embodiment, an image processing apparatus including calculating circuitry having the same function as the calculating function 33a may calculate a correction value. In such a case, the calculating circuitry of the image processing apparatus acquires, for example, the detection signal detected with the reference detection element, and the detection signal detected with each of the X-ray detection elements to be calibrated, from the X-ray CT apparatus. In addition, the calculating circuitry of the image processing apparatus calculates the energy value in the feature point from the detection signal detected with the reference detection signal, and specifies the peak value of the feature point from the detection signal detected with the X-ray detection element to be calibrated. The calculating circuitry of the image processing apparatus calculates the correction value for each of the detection elements by linear regression using the first feature point and the second feature point.

The embodiments described above illustrate the structure of calculating a correction value by linear regression using the first feature point and the second feature point, but the embodiments are not limited thereto. For example, the number of feature points used for calculation of the correction value may be two or more. In addition, the embodiments described above illustrate the structure in which the correction value is calculated by linear regression, but the embodiments are not limited thereto. For example, when the number of feature points is three or more, the calculating function 33a may approximate a nonlinear function using the feature point to calculate the correction value.

In addition, the image processing apparatus may further include spectrum preprocessing circuit having the same function as the spectrum preprocessing function 33c according to the third embodiment. In such a case, the calculating circuitry of the image processing apparatus calculates, for example, the energy value in the feature point from the X-ray spectrum detected with the reference detection element and subjected to preprocessing.

The first embodiment to the third embodiment illustrate the case where the X-ray CT apparatus reconstructs an X-ray CT image, but the embodiments are not limited thereto. For example, reconstruction of the X-ray CT image may be executed in an apparatus other than the X-ray CT apparatus, as long as the apparatus is capable of acquiring raw data collected with the X-ray CT apparatus. For example, the image processing apparatus calibrates the detection signal collected with the X-ray CT apparatus for each of the X-ray detection elements on the basis of the correction value, and reconstructs the X-ray CT image using the calibrated detection signals.

In addition, the functions of the waveform shaping circuitry 143 and the function of the image reconstruction circuitry 36 explained in the first embodiment to the third embodiment may be achieved with software. For example, the functions of the waveform shaping circuitry 143 and the function of the image reconstruction circuitry 36 are achieved by causing a computer to execute an image processing program defining the process of the processing explained as the process to be executed with the waveform shaping circuitry 143 and the image reconstruction circuitry 36 in the above embodiments. The image processing program is stored in, for example, a hard disk or a semiconductor memory device, and read and executed with a processor such as a CPU and an MPU. The image processing program may be recorded and distributed in a computer-readable recording medium, such as a compact disc-read only memory (CD-ROM), a magnetic optical disk (MO), and a digital versatile disc (DVD). The image processing program may cause the computer to further execute the process of the processing explained as a process to be executed with the calculating function 33a according to the first embodiment to the third embodiment. In the same manner, software may achieve the functions of the movement control function 33b explained in the second embodiment and the spectrum preprocessing function 33c explained in the third embodiment.

The embodiments described above illustrate an X-ray CT apparatus as an example of the X-ray diagnostic apparatus, but the embodiments are not limited thereto. For example, the embodiments described above are also applicable to a mammography apparatus or an X-ray diagnostic apparatus including a photon counting X-ray detector.

The term "processor" used in the explanation described above means a circuit such as a central processing unit (CPU), a graphics processing unit (GPU), an application specific integrated circuit (ASIC), or a programmable logic device (such as a simple programmable logic device: SPLD, a complex programmable logic device: CPLD, and a field programmable gate array: FPGA). The processor achieves the function by reading and executing the program incorporated in the circuit of the processor. Instead of incorporating a program in the circuit of the processor, the apparatus may have a structure in which the program is stored in the storage circuitry included in the console 30. In this case, the processor achieves the function by reading and executing the program stored in the storage circuitry. The processors in the present embodiment are not limited to the case in which each of the processors is configured as a single circuit, but plurality of independent circuits may be combined to be configured as one processor, to achieve the functions. In addition, the constituent elements in FIG. 1 may be integrated into one processor, to achieve the functions.

In the explanation of the embodiments described above, the constituent elements of the illustrated devices are functional and conceptual ones, and are not necessarily configured physically as illustrated. For example, the calculating function 33a and the waveform shaping circuitry 143 may be integrated into a "correction unit". Specifically, the specific form of distribution and integration of the devices are not limited to those illustrated, but all or part of them may be functionally or physically distributed or integrated, according to various loads and/or use circumstances. In addition, all or desired part of the processing functions performed in the devices may be achieved with a CPU and programs analyzed and executed with the CPU, or may be achieved as hardware by wired logic.

The control method explained in the embodiments described above may be achieved by executing a control program prepared in advance, with a computer such as a personal computer and a work station. The control program may be distributed through a network such as the Internet. The control program may also be recorded on a computer-readable recording medium such as a hard disk drive, a flexible disk (FD), a CD-ROM, a MO, and a DVD, and executed by being read from the recording medium with a computer.

At least one of the embodiments described above enables accurate and simple calibration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray image diagnostic apparatus comprising:
    a photon counting X-ray detector including a plurality of detection elements each of which is configured to detect X-rays and output a detection signal;
    calibration circuitry configured to calculate a feature point in an energy spectrum for each of the plurality of detection elements based on count values of the plurality of signals output from the plurality of detection elements and corresponding to respective X-ray application conditions relating to continuous X-rays, wherein the respective X-ray application conditions differ in at least one of a tube voltage and a tube current, calculate a correction value for each of the plurality of detection elements on the basis of the feature point, and calibrate the detection signal of each of the plurality of detection elements using the correction value; and
    image generating circuitry configured to generate an image using the calibrated detection signals of the plurality of detection elements.

2. The X-ray image diagnostic apparatus according to claim 1, wherein the calibration circuitry specifies a peak value among the plurality of signals at which a ratio of a count value of a first signal to a count value of a second signal has a predetermined value as the feature point.

3. The X-ray image diagnostic apparatus according to claim 2, wherein the calibration circuitry specifies the feature point from a peak value of a period in which the plurality of signals monotonously increases or monotonously decreases.

4. The X-ray image diagnostic apparatus according to claim 3, wherein the calibration circuitry specifies the feature point from a peak value at which a change quantity of a count value of one of the plurality of signals is maximum.

5. The X-ray image diagnostic apparatus according to claim 1, wherein the calibration circuitry specifies a peak value among the plurality of signals at which a count value of a first signal collected under presence of a filter removing X-rays of a predetermined band is equal to a count value of a second signal collected under absence of the filter, as the feature point.

6. The X-ray image diagnostic apparatus according to claim 5, wherein the filter removes X-rays including a peak value at which the first signal has a peak as the predetermined band.

7. The X-ray image diagnostic apparatus according to claim 1, wherein the calibration circuitry calculates the correction value by linear regression using a first feature point specified from a first signal and a second signal with a first X-ray application condition and a second feature point specified from the first signal and the second signal with a second X-ray application condition.

8. The X-ray image diagnostic apparatus according to claim 7, wherein the calibration circuitry determines an energy value of the first feature point and an energy value of the second feature point using X-ray spectrum derived in advance for each of the X-ray application conditions, to calculate the correction value.

9. The X-ray image diagnostic apparatus according to claim 7, wherein the calibration circuitry determines an energy value of the first feature point and an energy value of the second feature point from a plurality of signals detected with a reference detection element having energy resolution higher than that of the plurality of detection elements included in the photon counting X-ray detector, to calculate the correction value.

10. The X-ray image diagnostic apparatus according to claim 9, further comprising
    movement control circuitry configured to control movement of the photon counting X-ray detector in a channel direction independently of an X-ray tube, and perform control such that a position of the reference detection element in the channel direction at the time when the energy value of the first feature point and the energy value of the second feature point are determined agrees with a position of the detection element to be calibrated in the channel direction at the time when the first feature point and the second feature point are specified from a plurality of signals detected with the detection element to be calibrated.

11. The X-ray image diagnostic apparatus according to claim 10, wherein the movement control circuitry positions the reference detection element in a position opposed to the X-ray tube when the energy value of the first feature point and the energy value of the second feature point are determined, and positions the detection element to be calibrated in the position opposed to the X-ray tube when the first feature point and the second feature point are specified from the plurality of signals detected with the detection element to be calibrated.

12. The X-ray image diagnostic apparatus according to claim 10, wherein the movement control circuitry positions the reference detection element in a position agreeing with a relative position between the detection element to be calibrated and the X-ray tube in a state in which a center of the photon counting X-ray detector is opposed to the X-ray tube when the energy value of the first feature point and the energy value of the second feature point are determined, and positions the center of the photon counting X-ray detector in the position opposed to the X-ray tube when the first feature point and the second feature point are specified from the plurality of signals detected with the detection element to be calibrated.

13. The X-ray image diagnostic apparatus according to claim 9, wherein the photon counting X-ray detector includes the reference detection element in at least part of the plurality of detection elements.

14. The X-ray image diagnostic apparatus according to claim 1, wherein the photon counting X-ray detector is an area detector.

15. The X-ray image diagnostic apparatus according to claim 1, further comprising:
preprocessing circuitry configured to preprocess the plurality of signals, wherein the calibration circuitry calibrates the detection signal of each of the detection elements using the correction value calculated from the preprocessed signals.

16. The X-ray image diagnostic apparatus as claimed in claim 1, wherein the respective X-ray application conditions have a same tube voltage but different tube currents.

17. The X-ray image diagnostic apparatus as claimed in claim 1, wherein the respective X-ray application conditions have a same tube current but different tube voltages.

18. A method comprising:
calculating a feature point in an energy spectrum for each of a plurality of detection elements (1) included in a photon counting X-ray detector and (2) configured to (2a) detect X-rays and (2b) output a detection signal, the feature point corresponding to respective X-ray application conditions relating to continuous X-rays, wherein the respective X-ray application conditions differ in at least one of a tube voltage and a tube current;
calculating a correction value for each of the plurality of detection elements on the basis of the feature point;
calibrating the detection signal of each of the plurality of detection elements using the correction value; and
generating an image using the calibrated detection signals of the plurality of detection elements.

19. The method as claimed in claim 18, wherein the respective X-ray application conditions have a same tube voltage but different tube currents.

20. The method as claimed in claim 18, wherein the respective X-ray application conditions have a same tube current but different tube voltages.

21. An X-ray image diagnostic comprising:
a photon counting X-ray detector including a plurality of detection elements each of which is configured to detect X-rays and output a detection signal;
calibration circuitry configured to (1) calculate a feature point in an energy spectrum based on count values of a plurality of signals output from the plurality of detection elements and (2) calibrate the detection signal of each of the plurality of detection elements using a correction value calculated using the feature point and from the plurality of signals output from the plurality of detection elements and corresponding to respective X-ray application conditions relating to continuous X-rays; and
image generating circuitry configured to generate an image using the calibrated detection signals of the plurality of detection elements,
wherein the calibration circuitry specifies as the feature point a peak value among the plurality of signals at which a ratio of a count value of a first signal to a count value of a second signal has a predetermined value.

22. An X-ray image diagnostic comprising:
a photon counting X-ray detector including a plurality of detection elements each of which is configured to detect X-rays and output a detection signal;
calibration circuitry configured to (1) calculate a feature point in an energy spectrum based on count values of a plurality of signals output from the plurality of detection elements and (2) calibrate the detection signal of each of the plurality of detection elements using a correction value calculated using the feature point and from the plurality of signals output from the plurality of detection elements and corresponding to respective X-ray application conditions relating to continuous X-rays; and
image generating circuitry configured to generate an image using the calibrated detection signals of the plurality of detection elements,
wherein the calibration circuitry specifies a peak value among the plurality of signals at which a count value of a first signal collected under presence of a filter removing X-rays of a predetermined band is equal to a count value of a second signal collected under absence of the filter, as he feature point.

23. An X-ray image diagnostic comprising:
a photon counting X-ray detector including a plurality of detection elements each of which is configured to detect X-rays and output a detection signal;
calibration circuitry configured to (1) calculate a feature point in an energy spectrum based on count values of a plurality of signals output from the plurality of detection elements and (2) calibrate the detection signal of each of the plurality of detection elements using a correction value calculated using the feature point and from the plurality of signals output from the plurality of detection elements and corresponding to respective X-ray application conditions relating to continuous X-rays; and
image generating circuitry configured to generate an image using the calibrated detection signals of the plurality of detection elements,
wherein the calibration circuitry calculates the correction value by linear regression using a first feature point specified from a first signal and a second signal with a first X-ray application condition and a second feature point specified from the first signal and the second signal with a second X-ray application condition.

* * * * *